United States Patent
Souls et al.

(10) Patent No.: US 11,229,430 B2
(45) Date of Patent: Jan. 25, 2022

(54) SYSTEMS, DEVICES AND METHODS OF USING NEEDLE SHEATHS FOR PASSING CURVED, SUPERELASTIC SUTURE NEEDLES THROUGH TROCARS

(71) Applicant: Ethicon, Inc., Somerville, NJ (US)

(72) Inventors: Doug Souls, Andover, NJ (US); Christophe Vailhe, Hillsborough, NJ (US); Alexander M. Cannara, Roseland, NJ (US); Noha Elmouelhi, Whitehouse Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 50 days.

(21) Appl. No.: 16/535,383

(22) Filed: Aug. 8, 2019

(65) Prior Publication Data

US 2021/0038216 A1 Feb. 11, 2021

(51) Int. Cl.
*A61B 17/04* (2006.01)
*A61B 17/06* (2006.01)
*A61B 17/34* (2006.01)

(52) U.S. Cl.
CPC .... *A61B 17/0469* (2013.01); *A61B 17/06066* (2013.01); *A61B 17/3421* (2013.01); *A61B 17/0482* (2013.01); *A61B 17/06166* (2013.01); *A61B 17/3478* (2013.01)

(58) Field of Classification Search
CPC .......... A61B 17/0469; A61B 17/06066; A61B 17/3421; A61B 17/0493
See application file for complete search history.

(56) References Cited

U.S. PATENT DOCUMENTS

| 5,219,358 | A |   | 6/1993 | Bendel et al. |
|-----------|---|---|--------|---------------|
| 5,741,299 | A | * | 4/1998 | Rudt ................... A61B 17/0493 606/224 |
| 5,904,690 | A | * | 5/1999 | Middleman ............... B25B 9/00 606/113 |
| 5,908,426 | A |   | 6/1999 | Pierce |

(Continued)

FOREIGN PATENT DOCUMENTS

| CN | 201958934 | 9/2011 |
| CN | 201958941 | 9/2011 |

(Continued)

OTHER PUBLICATIONS

International Search Report issued by the International Searching Authority in corresponding International Application No. PCT/IB2020/057449, dated Nov. 6, 2020, 5 pages.

*Primary Examiner* — Tuan V Nguyen

(57) ABSTRACT

A needle sheath includes a tubular shaft having a chamfered edge at a distal end thereof. A stop flange is secured to a proximal end of the tubular shaft. A needle relief slot is formed in a bottom side of the tubular shaft. The needle relief slot has a length that extends along an axis that is parallel to the longitudinal axis of the tubular shaft. A needle point slot formed in a top side of the tubular shaft. The needle point slot has a length that extends along an axis that is perpendicular to both the longitudinal axis of the tubular shaft and the needle relief slot axis. A suture needle is disposed within the tubular shaft of the needle sheath. The suture needle has a curved body that passes through the needle relief slot and a needle point captured within the needle point slot.

22 Claims, 21 Drawing Sheets

(56) References Cited

U.S. PATENT DOCUMENTS

| | | | |
|---|---|---|---|
| 6,113,610 A * | 9/2000 | Poncet | A61B 17/0469 |
| | | | 606/139 |
| 6,527,793 B1 | 3/2003 | Valtchev | |
| 6,730,061 B1 | 5/2004 | Cuschieri et al. | |
| 7,083,687 B2 | 8/2006 | Tanaka et al. | |
| 7,270,720 B2 | 9/2007 | Brhel et al. | |
| 7,727,257 B2 | 6/2010 | Loubens et al. | |
| 7,922,744 B2 | 4/2011 | Morris et al. | |
| 8,308,764 B2 | 11/2012 | Loubens et al. | |
| 8,784,382 B2 | 7/2014 | McGuckin et al. | |
| 8,915,932 B2 | 12/2014 | Pipenhagen et al. | |
| 9,610,075 B2 | 4/2017 | Heneveld | |
| 2003/0233101 A1* | 12/2003 | Lubock | A61B 90/39 |
| | | | 606/116 |
| 2011/0125108 A1 | 5/2011 | Deviere et al. | |
| 2011/0172706 A1 | 7/2011 | Kappel et al. | |
| 2016/0193023 A1 | 7/2016 | Pereira et al. | |
| 2016/0281199 A1 | 9/2016 | Loubens | |
| 2016/0338696 A1 | 11/2016 | Loubens | |
| 2017/0252038 A1 | 9/2017 | Callaghan et al. | |
| 2017/0273706 A1* | 9/2017 | Mirza | A61B 17/3211 |

FOREIGN PATENT DOCUMENTS

| | | |
|---|---|---|
| CN | 102551830 | 7/2012 |
| CN | 204410871 | 6/2015 |
| DE | 102004012680 | 11/2005 |
| EP | 2781194 | 9/2014 |
| WO | 9508296 | 3/1995 |

\* cited by examiner

SYSTEMS, DEVICES AND METHODS OF USING NEEDLE SHEATHS FOR PASSING CURVED, SUPERELASTIC SUTURE NEEDLES THROUGH TROCARS

BACKGROUND OF THE INVENTION

Field of the Invention

The present patent application is generally related to surgical procedures and surgical tools, and is more specifically related to curved, elastically deformable suture needles used for suturing tissue.

Description of the Related Art

Sutures are used to approximate tissue that has been separated during a surgical procedure or due to an accident or trauma. Instruments used for suturing tissue typically include a suture needle and a trailing length of suture thread that is attached to an end of the suture needle.

In order to minimize patient trauma during minimally invasive surgical (MIS) procedures, many efforts have been directed to reducing the size (e.g., diameter) of the trocars and cannulas (hereinafter commonly referred to as trocars) that are inserted into patients. When a surgical procedure requires suturing tissue, a problem arises in the types of needle and suture assemblies that can be delivered through the trocar to the surgical site. Many surgeons prefer to use curved needles, which are typically in the range of ¼ to ⅝ of a circle (i.e., an arc whose interior angle is in the range of about 90 degrees-225 degrees). Curved needles having these dimensions require the trocar to be large enough to accommodate the arc of the needle, which in many procedures is not feasible because the preferred curved surgical needle cannot pass through the preferred, narrower, trocar to reach the surgical site.

In an effort to resolve the above-noted size problems, advances have been made to provide surgical needles made of superelastic alloys that elastically deflect or straighten when passed through a trocar and then return back to the original curved shape when removed from the trocar at the surgical site.

One well-known superelastic alloy used to make needles having superelastic properties is the Ni—Ti alloy, which is commonly referred to as Nitinol. The superelastic properties are due to a stress-induced martensitic phase change that takes place in certain alloys above their transformation temperature. The martensite reverts immediately to undeformed austenite as soon as the stress is removed providing a very springy "rubberlike" elasticity in these alloys.

A suture needle produced from a superelastic alloy exhibiting a curvature much larger than can be normally accommodated by a small diameter trocar can flex into a predominantly straight or flatter shape as it is pushed or pulled through the smaller trocar into the surgical site. After the needle has passed through the trocar and reaches the surgical site, the superelastic properties of the needle will return the needle back to its original curved configuration.

Upon returning to the original curved configuration, the suture needle may be used to complete a suturing operation. At the end of the suturing operation, the curved suture needle is removed from the patient by withdrawing the needle through the smaller trocar opening. During withdrawal, the curved needle straightens or flattens for passing through the smaller diameter trocar.

In spite of the above advances, there remains a need for improved systems, devices and methods for passing curved suture needles made of elastically deformable materials (e.g., Nitinol) through smaller trocars.

SUMMARY OF THE INVENTION

In one embodiment, the systems, devices and methods disclosed herein enable larger curved, elastically deformable suture needles to be used in laparoscopic and robotic surgeries to provide surgeons with greater bite width and depth than previously possible. For example, CTX needles made of elastically deformable materials (e.g., Nitinol) may be used with trocars as small as 5 mm, which provides a dramatic improvement over conventional stainless steel needles that must be permanently deformed to enable trocar passage.

Using smaller diameter trocars (e.g., 5 mm trocars) may reduce pain, and lower the risk of infection, hernia and other surgical complications. As a result, larger needles such as CTX, CT, CT-1, and SH needles may be used with 5 mm trocars, whereas before they were limited to use with 8, 10, 12, or 15 mm trocars.

At present, when using conventional stainless steel needles, surgeons are required to bend or reshape the stainless steel needles to pass the needles through smaller trocars. Once inside the body, the surgeons must re-bend or reshape the needles back to their original, usable shape, if possible.

The superelastic curved suture needles disclosed herein eliminate the need for the surgeon to re-bend or reshape the needle, which saves time and frustration when seeking to obtain a usable curvature. Once a surgical procedure is completed, the surgeon will not need to bend the needle again to remove it through the trocar.

In one embodiment, a needle sheath preferably includes a tubular shaft having a proximal end, a distal end, and a longitudinal axis that extends from the proximal end to the distal end of the tubular shaft.

In one embodiment, the tubular shaft is hollow and includes a proximal opening located at the proximal end of the tubular shaft, a distal opening located at the distal end of the tubular shaft, and an elongated conduit that extends between the proximal and distal openings.

In one embodiment, the distal end of the tubular shaft desirably includes a chamfered edge. In one embodiment, the chamfered edge may be located on a bottom side of the tubular shaft.

In one embodiment, a needle relief slot is formed in the bottom side of the tubular shaft. The needle relief slot may be proximal to the chamfered edge. The needle relief slot may have a length that extends along an axis that is parallel with the longitudinal axis of the tubular shaft. In one embodiment, the axis of the needle relief slot intersects with the chamfered edge of the tubular shaft.

In one embodiment, the tubular shaft desirably includes a cylindrical shaped outer wall defining inner and outer surfaces. In one embodiment, the needle relief slot is formed in the cylindrical shaped outer wall and extends from the inner surface to the outer surface of the cylindrical shaped outer wall.

In one embodiment, the needle sheath preferably includes a needle point slot formed in a top side of the tubular shaft. In one embodiment, the needle point slot opposes the needle relief slot that is formed in the bottom side of the tubular shaft. In one embodiment, the needle point slot is distal to the needle relief slot. In one embodiment, the needle point slot has a length that extends along an axis that is perpendicular to the longitudinal axis of the tubular shaft.

In one embodiment, the needle point slot may be an opening that is formed in the tubular shaft and that extends completely through the outer wall of the tubular shaft. In one embodiment, the needle point slot may be a depression or groove formed in the inner surface of the tubular shaft, and which does not extend completely through the outer wall of the tubular shaft.

In one embodiment, a stop flange may be secured to the proximal end of the tubular shaft for controlling and/or limiting the insertion of the needle sheath into a trocar.

In one embodiment, a suture needle may be disposed within the tubular shaft of the needle sheath. In one embodiment, the suture needle may be made of an elastically deformable material to enable it to pass through trocars (e.g., of about 5 mm, 8 mm, 10 mm, or 12 mm). In one embodiment, the suture needle may be made of hyper-elastic or superelastic materials such as Nitinol.

In one embodiment, the suture needle desirably includes an elongated body having a curved shape. In one embodiment, the elongated body desirably has a proximal end, a distal end, and a curved mid-section located between the proximal and distal ends. In one embodiment, a suture thread may be attached to the proximal end, and the distal end may taper to a sharpened point.

In one embodiment, a curved suture needle may deform elastically during trocar insertion so that it can pass through a trocar having a smaller inner diameter than the bite depth of the curved suture needle. Thus, the suture needle is able to deform elastically during trocar insertion, and transform back to its original curved shape once it has passed through the trocar.

In one embodiment, when the suture needle is pulled into the distal end of the needle sheath (e.g., by pulling on an attached suture thread), the suture needle preferably has a curved body that is disposed within the needle relief slot and a needle point that is disposed within the needle point slot.

In one embodiment, the suture needle may be pulled into a distal end of a needle sheath so that the curved body portion of the suture needle passes through the needle relief slot and extends outside the tubular shaft, whereby the suture needle defines a first height that is greater than a cross-sectional diameter of the tubular shaft of the needle sheath.

In one embodiment, the suture needle may be made of a superelastic material that enables the curved body of the suture needle to transform from a curved configuration having the first height to a flatter and/or straighter configuration having a second height that is less than the first height. When at the second height, the suture needle preferably has a height that is less than or equal to an inner diameter of the tubular shaft of the needle sheath.

In one embodiment, a system may include a needle driver that is disposable within the elongated conduit of the tubular shaft of the needle sheath for engaging the suture needle. In one embodiment, the needle driver preferably includes clamping jaws adapted to secure the suture needle and/or the suture thread secured to the proximal end of the suture needle.

In one embodiment, the clamping jaws may grasp a tapered distal end of a suture needle that is close to the needle point without damaging or dulling the point. In one embodiment, the clamping jaws of the needle driver preferably surround, encapsulate and/or protect the point as the suture needle passes through the needle sheath for protecting the needle point from damage.

In one embodiment, the tubular shaft has a first outer diameter, and the stop flange has a second outer diameter that is greater than the first outer diameter of the tubular shaft.

In one embodiment, the needle sheath may be made of durable, biocompatible materials such as polymers and metals (e.g., stainless steel)

In one embodiment, a needle sheath may include a tubular shaft having a proximal end, a distal end with a chamfered edge, and a longitudinal axis extending between the proximal and distal ends of the tubular shaft.

In one embodiment, a flange is secured to the proximal end of the tubular shaft. In one embodiment, the flange has an outer dimension that is greater than a cross-sectional diameter of the tubular shaft.

In one embodiment, the needle sheath preferably includes a needle relief slot formed in a bottom side of the tubular shaft. In one embodiment, the needle relief slot desirably has a length that extends along a needle relief slot axis that is parallel to the longitudinal axis of the tubular shaft and that passes through the chamfered edge.

In one embodiment, the needle sheath preferably includes a needle point slot formed in a top side of the tubular shaft that is distal to the needle relief slot. In one embodiment, the needle point slot desirably has a length that extends along a needle point slot axis that is perpendicular to both the longitudinal axis of the tubular shaft and the needle relief slot axis of the needle relief slot.

In one embodiment, a suture needle may be disposed within the tubular shaft of the needle sheath. In one embodiment, the suture needle has a curved body section that is disposed within the needle relief slot with the needle point disposed within the needle point slot.

In one embodiment, after the suture needle has been pulled into a distal end of the needle driver, a curved body portion of the suture needle desirably passes through the needle relief slot for extending outside the tubular shaft of the needle sheath. The curved body of the suture needle desirably defines a first height that is greater than the cross-sectional diameter of the inner surface of the tubular shaft.

In one embodiment, the suture needle may be made of a superelastic material that enables the suture needle to transform from a curved configuration having the first height to a straighter and/or flatter configuration having a second height that is less than the first height. In one embodiment, the second height is desirably less than or equal to an inner diameter of the tubular shaft of the needle sheath.

In one embodiment, a suture thread may be secured to a proximal end of the suture needle.

In one embodiment, a needle driver may be disposed within the tubular shaft of the needle sheath. In one embodiment, the needle driver preferably includes clamping jaws in contact with at least one of the suture needle and the suture thread secured to the proximal end of the suture needle for passing the suture needle through the needle sheath.

In one embodiment, a method of loading a curved suture needle into a needle sheath may include juxtaposing a curved suture needle with a distal end of a needle sheath. The suture needle may be made of elastically deformable or superelastic materials.

In one embodiment, the needle sheath preferably includes a tubular shaft having a proximal end, a distal end with a chamfered edge, a longitudinal axis extending between the proximal and distal ends, a needle relief slot formed in a bottom side of the tubular shaft having an axis that is parallel to the longitudinal axis of the tubular shaft and that passes through the chamfered edge, and a needle point slot formed in a top side of the tubular shaft that is distal to the needle relief slot and that extends along an axis that is perpendicular to both the longitudinal axis of the tubular shaft and the axis of the needle relief slot.

In one embodiment, a proximal end of the curved suture needle is preferably pulled into the distal end of the tubular shaft so that a curved body portion of the curved suture needle passes through the needle relief slot and a distal point of the curved suture needle is disposed within the needle point slot.

In one embodiment, the needle sheath may be used for delivering an elastically deformable suture needle to a surgical site.

In one embodiment, the needle sheath may be slid over a needle driver (e.g., a 5 mm needle driver) having clamping jaws at a distal end thereof.

In one embodiment, the clamping jaws of the needle driver may be used grasp the suture needle at a location on the suture needle that is just proximal to the needle point, whereby the needle point is positioned within the profile of the needle driver jaws and whereby the barrel of the suture needle is in-line with the longitudinal axis of the needle driver.

In one embodiment, after the suture needle has been grasped by the needle driver, the needle sheath is slid over the suture needle in an orientation that prevents the suture needle from engaging with the needle relief slot and the needle point slot so that the suture needle is completely captured within the lumen of the needle sheath.

In one embodiment, the needle sheath containing the suture needle and the attached suture thread may be slid into a trocar by pushing the needle driver until a stop flange of the needle sheath contacts a proximal end of a trocar.

In one embodiment, the needle driver may be pushed distally until the suture needle exits the distal end of the needle sheath, whereupon the suture needle is positioned at a surgical site inside a patient and is ready and available for use.

In one embodiment, after a surgical procedure has been completed, the suture needle may be removed from a surgical site. In one embodiment, the needle driver may be used to grab the suture thread and pull the suture thread and the suture needle into the needle sheath.

In one embodiment, the chamfered end of the needle sheath serves to automatically rotate and/or orient the suture needle so that a curved portion of the suture needle is aligned with the needle relief slot. The needle relief slot on the needle sheath allows the suture needle to enter the needle sheath with minimal distortion. Once the suture needle is fully within the needle sheath, the needle point is preferably captured in the needle point slot. Capturing the needle point in the needle point slot serves to prevent the needle from moving distally (i.e., back into the surgical site).

In one embodiment, the needle point slot may be formed through the full thickness of the tubular wall of the needle sheath or may be a recess or depression formed in the inner surface of the tubular wall of the needle sheath.

In one embodiment, the length of the needle relief slot and its relative axial location with respect to the needle point slot is designed to match the particular geometry of the suture needle that will be passed through the needle sheath. In other words, the length of the needle relief slot and its axial location with respect to the needle point slot is a function of the needle curvature (e.g., degree of curvature and radius of curvature) and the inside diameter of the needle sheath.

In one embodiment, after the suture needle has been pulled into the distal end of the needle sheath so that the curved body of the suture needle is positioned in the needle relief slot and so that the needle point is located in the needle point slot, the needle driver may be used to further pull the suture needle by the suture thread into the needle sheath until the suture needle flexes and is positioned completely inside the sheath. At this stage of the removal process, the curved body of the suture needle no longer extends through the needle relief slot.

In one embodiment, the needle sheath with the captured suture needle may be removed from an opening at a proximal end of a trocar. In one embodiment, the needle driver, the suture thread, and the suture needle may be removed from a proximal end of the needle sheath by moving the needle driver (while still gripping the suture) in a proximal direction.

In one embodiment, a surgical tool that is configured for introducing and removing suture needles (e.g., curved suture needles) from surgical cavities preferably includes a tubular shaft having a proximal end with a proximal opening, a distal end with a distal opening, and a longitudinal axis that extends from the proximal end to the distal end of the tubular shaft. In one embodiment, the distal end of the tubular shaft desirably includes a chamfered edge located on a bottom side of the tubular shaft. In one embodiment, the surgical tool preferably includes a suture needle stop formed in a top side of the tubular shaft for preventing uncontrolled release of the suture needle from the distal opening at the distal end of the tubular shaft. In one embodiment, the suture needle stop may be formed in an inner surface of the tubular shaft and may oppose the chamfered edge of the tubular shaft.

In one embodiment, the surgical tool including the suture needle stop may include a trocar or a needle sheath.

In one embodiment, the surgical tool having the needle point stop formed in an inner surface of the tubular shaft may include a needle point slot having a tortuous path, a tapered notch, a stop ring that projects inwardly from the inner surface of the tubular shaft, and/or a stop bump that projects inwardly from the inner surface of the tubular shaft. In one embodiment, the needle point slot is adapted to engage and/or catch a needle point of a suture needle to prevent uncontrolled release of the suture needle from the distal end of the tubular shaft.

These and other preferred embodiments of the present patent application will be described in more detail below.

DETAILED DESCRIPTION OF PREFERRED EMBODIMENTS

Figure 1:
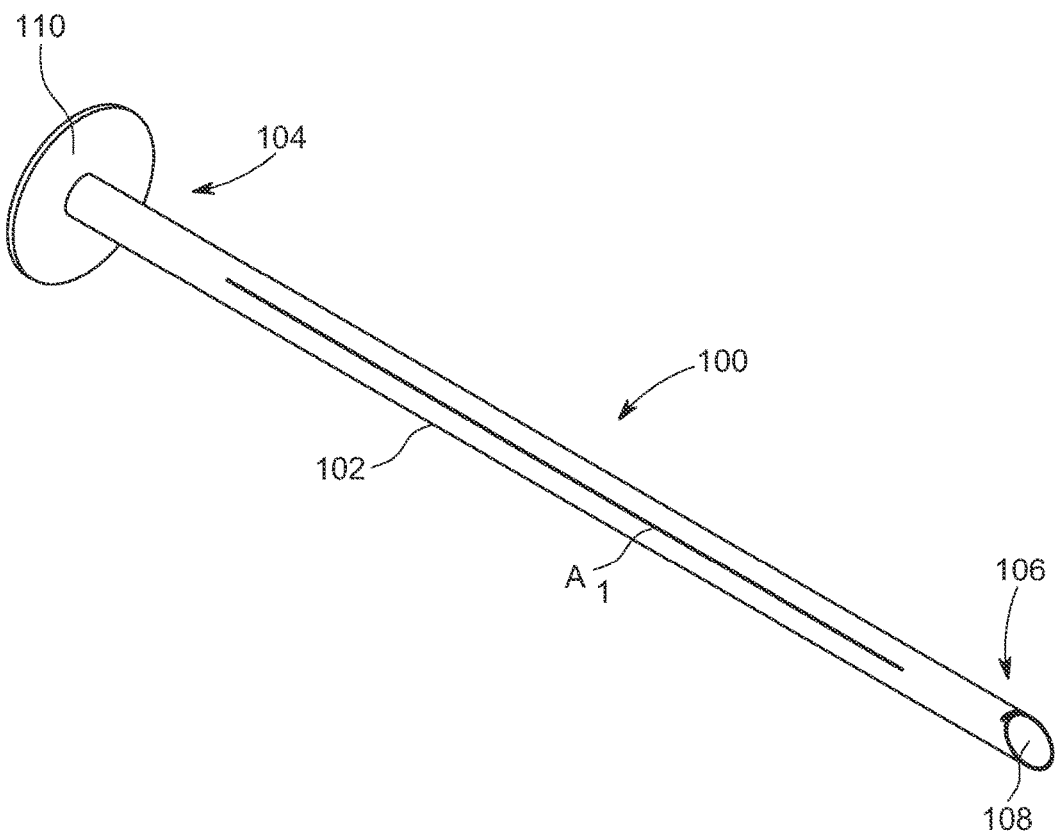
FIG. 1 is a perspective view of a needle sheath, in accordance with one embodiment of the present patent application.

Referring to FIG. 1, in one embodiment, a needle sheath 100 is configured for safely and effectively delivering a suture needle to a surgical site and, after completing a surgical procedure, withdrawing the suture needle from the surgical site for being removed from a patient's body. In one embodiment, the needle sheath 100 desirably includes a tubular shaft 102 (e.g., a hollow tube or lumen) having a proximal end 104 and a distal end 106. The tubular shaft 102 is preferably hollow for passing suture needles therethrough and desirably has an elongated conduit 108 that extends from the proximal end 104 to the distal end 106 thereof. In one embodiment, the needle sheath 100 desirably includes a flange 110 secured to the distal end 104 of the tubular shaft 102. In one embodiment, the flange 110 has a circular shape having a diameter that is greater than the cross-sectional diameter of the tubular shaft 102. The flange 110 may function as a stop flange to control and/or limit the depth of insertion of the tubular shaft 102 into a surgical instrument such as a trocar or cannula. The needle sheath may be made of rugged, biocompatible materials such as polymers and metals (e.g., stainless steel).

Figure 2A:
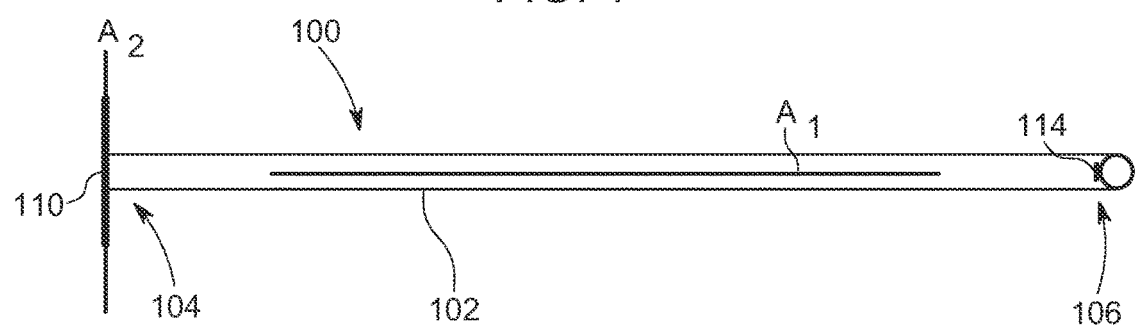
FIG. 2A is a top plan view of the needle sheath shown in FIG. 1.
Figure 2B:
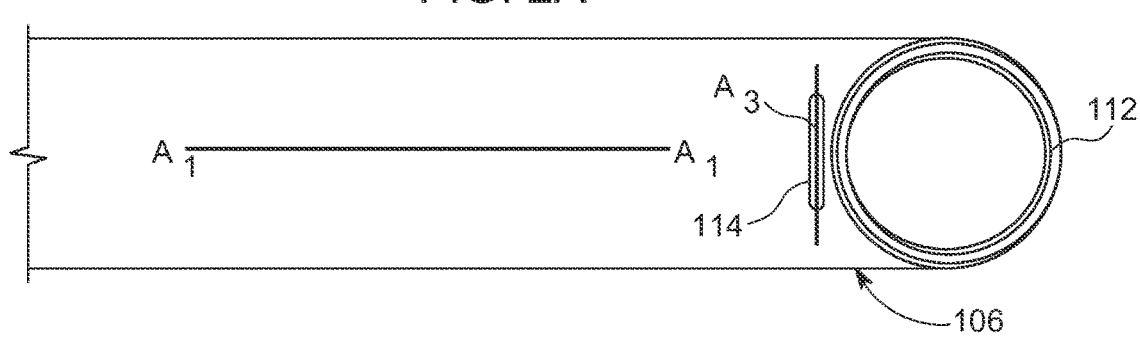
FIG. 2B is a magnified view of a distal end of the needle sheath shown in FIG. 2A.

Referring to FIGS. 1 and 2A-2B, in one embodiment, the needle sheath 100 preferably has a longitudinal axis $A_1$ that extends from the proximal end 104 to the distal end 106 of the tubular shaft 102. In one embodiment, the flange 110 located at the proximal end 104 of the tubular shaft 102 preferably extends along an axis $A_2$ that is perpendicular to the longitudinal axis $A_1$ of the needle sheath 100.

In one embodiment, the distal end 106 of the tubular shaft 102 desirably has a chamfered edge 112. In one embodiment, the chamfered edge 112 preferably defines a distal-most end of the tubular shaft 102 of the needle sheath 100. In one embodiment, the chamfered edge 112 is located at a bottom side of the tubular shaft 102.

In one embodiment, the needle sheath 100 desirably includes a needle point slot 114 that is formed in the top side of the tubular shaft 102. The needle point slot 114 may have a length defining a longitudinal axis $A_3$, which is perpendicular to the longitudinal axis $A_1$ of the needle sheath 100. In one embodiment, the chamfered edge 112 projects from the bottom side of the tubular shaft 102 and the needle point slot 114 is formed on the top side of the tubular shaft, whereby the needle point slot 114 is about 180 degrees away from the chamfered edge 112 about the circumference of the tubular shaft.

Figure 3A:
FIG. 3A is a bottom view of the needle sheath shown in FIG. 1.
Figure 3B:
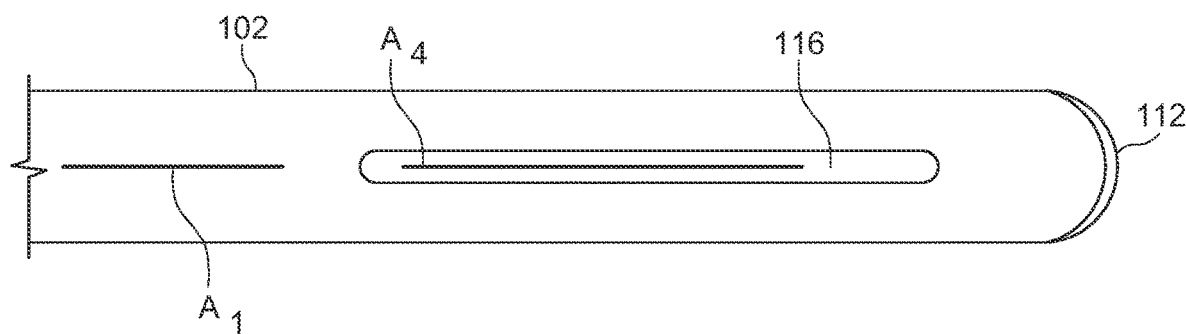
FIG. 3B is a magnified view of the distal end of the needle sheath shown in FIG. 3A.

Referring to FIGS. 3A and 3B, in one embodiment, the tubular shaft 102 of the needle sheath 100 preferably includes a needle relief slot 116 that is formed in the bottom side of the tubular shaft. In one embodiment, the needle relief slot 116 preferably opposes the needle point slot 114 shown and described above in FIGS. 2A and 2B. In one embodiment, the needle point slot is formed in the top side of the tubular shaft and the needle relief slot is formed in the bottom side of the tubular shaft, whereby the needle point slot and the needle relief slot are positioned about 180 degrees away from one another about the circumference of the tubular shaft. In one embodiment, the needle relief slot 116 desirably has a length defining a longitudinal axis $A_4$ that is co-axial with and/or parallel to the longitudinal axis $A_1$ of the tubular shaft 102 of the needle sheath 100. In one embodiment, the needle relief slot 116 is aligned with the chamfered edge 112 provided at the distal-most end of the tubular shaft 102. In one embodiment, both the needle relief slot 116 and the chamfered edge 112 are located at the bottom side of the tubular shaft 102, whereby the longitudinal axis $A_4$ of the needle relief slot 116 intersects and/or passes through the chamfered edge 112.

Figure 4:
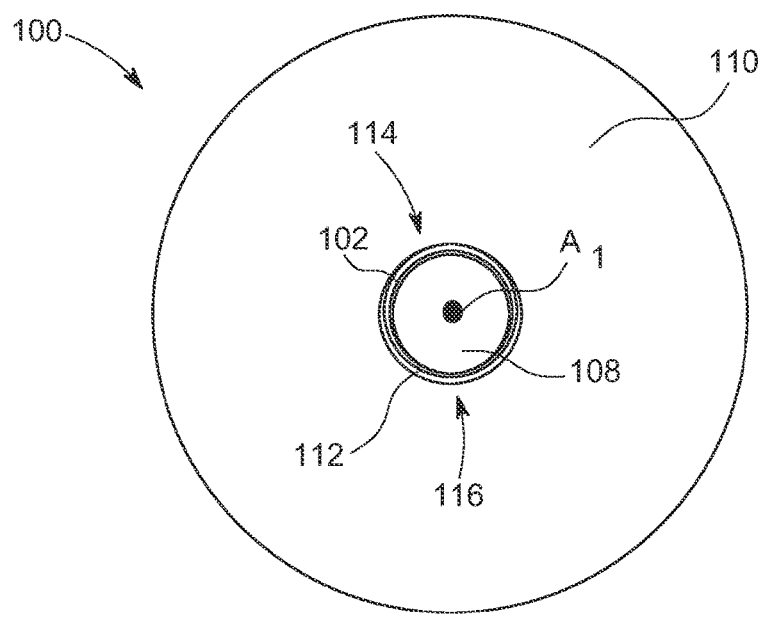
FIG. 4 is a distal end view of the needle sheath shown in FIG. 1.

Referring to FIG. 4, in one embodiment, the needle sheath 100 preferably includes the tubular shaft 102 that projects distally from the stop flange 110 located at the proximal end of the tubular shaft. In one embodiment, the needle point slot 114 is formed in the top side of the tubular shaft 102, and the needle relief slot 116 is formed in the bottom side of the tubular shaft 102. In one embodiment, the needle point slot 114 formed in the top side of the tubular shaft 102 is spaced 180 degrees away from the needle relief slot 116 formed in the bottom side of the tubular shaft 102. In one embodiment, the longitudinal axis of the needle relief slot 116 is in alignment with and/or intersects the chamfered edge 112 formed at the distal-most end of the tubular shaft 102. In one embodiment, the tubular shaft 102 has an elongated conduit 108 that extends along the longitudinal axis $A_1$ of the tubular shaft 102.

Figure 5:
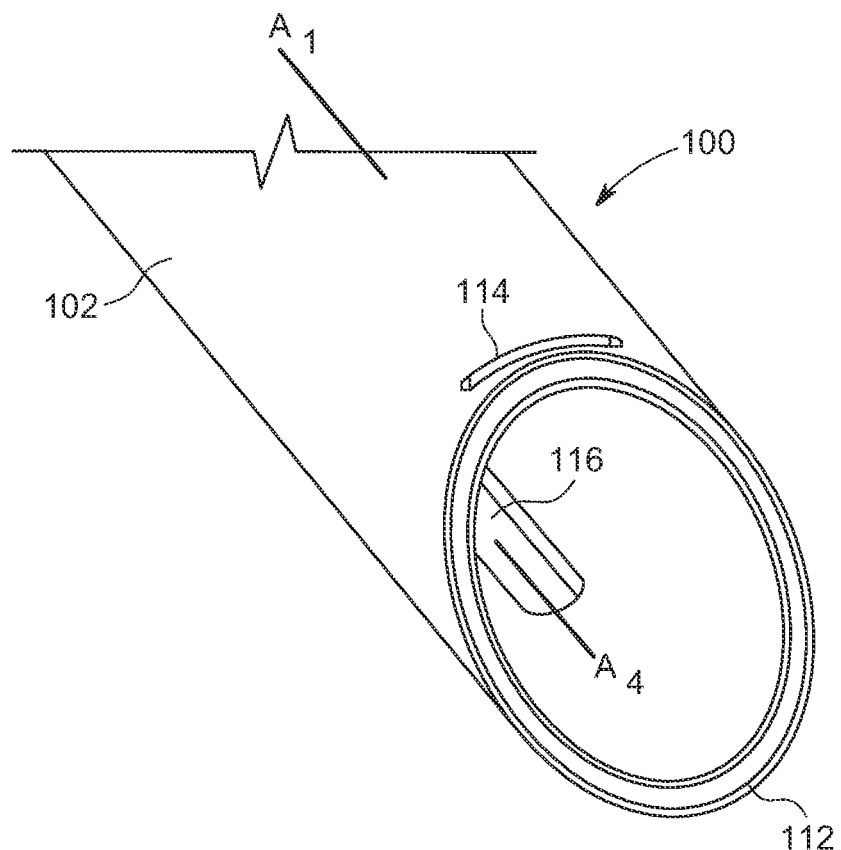
FIG. 5 is a perspective view of the distal end of the needle sheath shown in FIG. 1.
Figure 6:
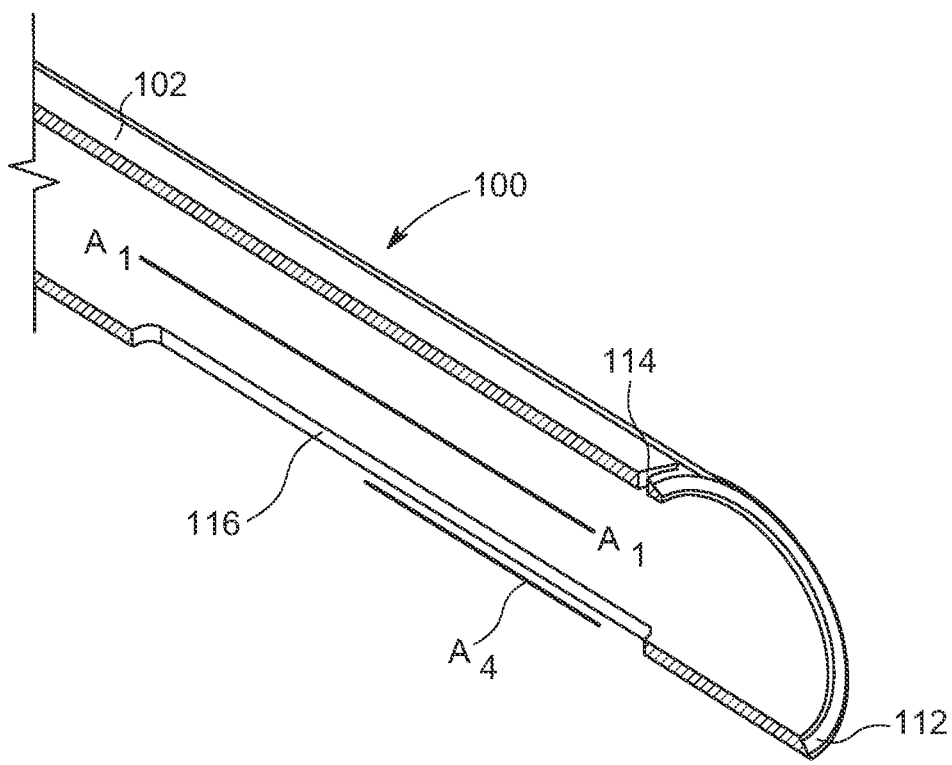
FIG. 6 is a cross-sectional view of the distal end of the needle sheath shown in FIG. 1.

Referring to FIGS. 5 and 6, in one embodiment, the needle point slot 114 is formed in the top side of the tubular shaft 102 of the needle sheath 100. The needle relief slot 116 is preferably formed in the bottom side of the tubular shaft 102 and has a longitudinal axis $A_4$ that is in axial alignment with the longitudinal axis $A_1$ of the tubular shaft 102. The longitudinal axis $A_4$ of the needle relief slot 116 formed in the bottom side of the tubular shaft 102 is also preferably in alignment with the chamfered edge 112 formed at the distal-most end of the tubular shaft 102. The needle relief slot 116 preferably extends along the longitudinal axis $A_4$, which is parallel with the longitudinal axis $A_1$ of the tubular shaft 102.

Figure 7A:
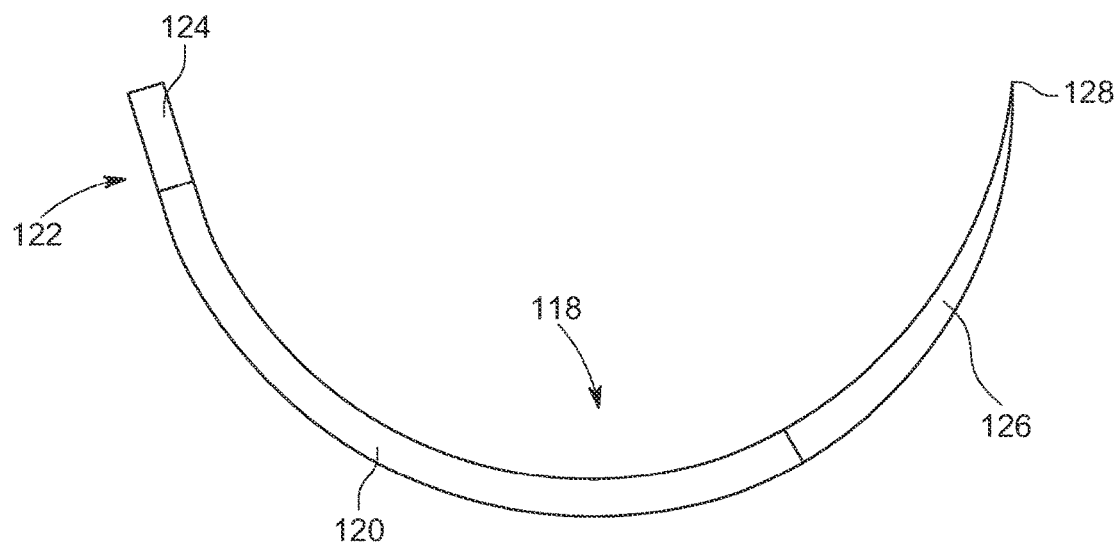
FIG. 7A is a side elevation view of a suture needle, in accordance with one embodiment of the present patent application.
Figure 7B:
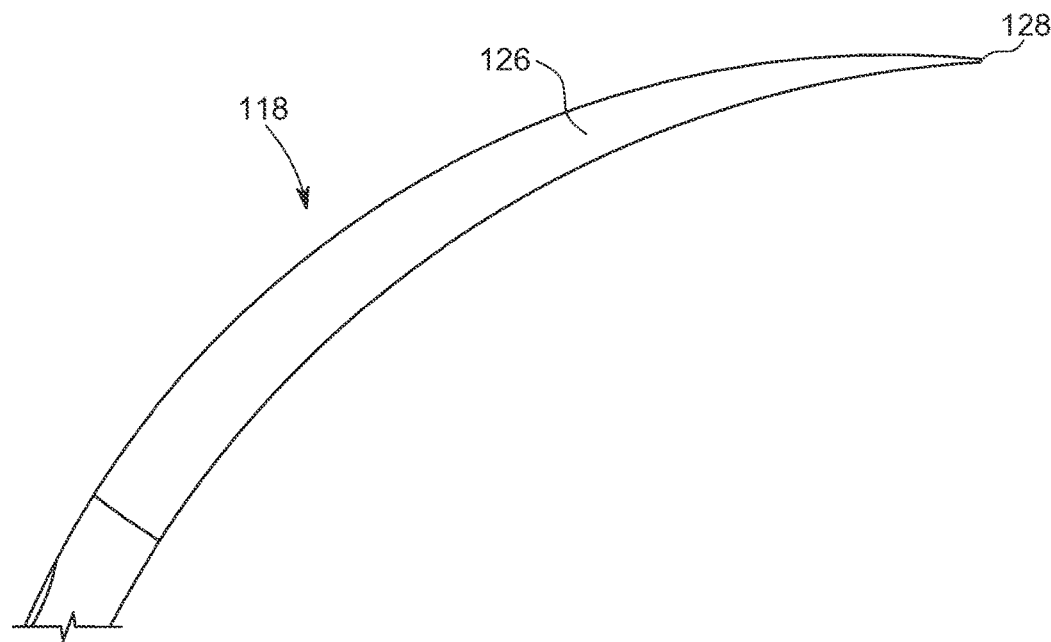
FIG. 7B is a magnified view of a distal end of the suture needle shown in FIG. 7A.

Referring to FIGS. 7A and 7B, in one embodiment, a suture needle 118, such as a suture needle made of elastic or superelastic materials (e.g., Nitinol), may be introduced into a surgical site and removed from the surgical site by passing the suture needle through the needle sheath 100 shown and described above in FIGS. 1-6. In one embodiment, the suture needle 118 preferably includes a curved body 120 having a proximal end 122 with a suture barrel 124 and a tapered distal end 126 including a sharpened point 128. In one embodiment, the suture needle 118 is preferably a curved suture needle adapted to be secured to a surgical suture. A suture thread may be secured to the suture barrel 124 located at the proximal end 122 of the suture needle 118.

The suture needle preferably has a curved shape (e.g., a half circle shape) that enables the suture needle to be efficiently passed through tissue during a suturing procedure. The curved suture needle may be placed under tension for flattening the suture needle for passing the needle through a needle sheath pr lumen having a smaller inner diameter than the normal height of the curved suture needle. The elastic and/or superelastic properties of the suture needle will enable the needle to transform back to the normal, curved shape upon being completely passed through the needle sheath.

In one embodiment, an end of a suture thread may be inserted into an opening provided in the suture barrel 124 and the suture barrel may be swaged and/or crimped for securing the suture to the proximal end 102 of the curved body 120. As will be described in more detail herein, the tapered distal end 126 of the suture needle may be engaged by the opposing clamping jaws of a needle driver for securing the suture needle to pass the suture needle through the needle sheath 100 shown and described above in FIGS. 1-6.

Figure 8A:
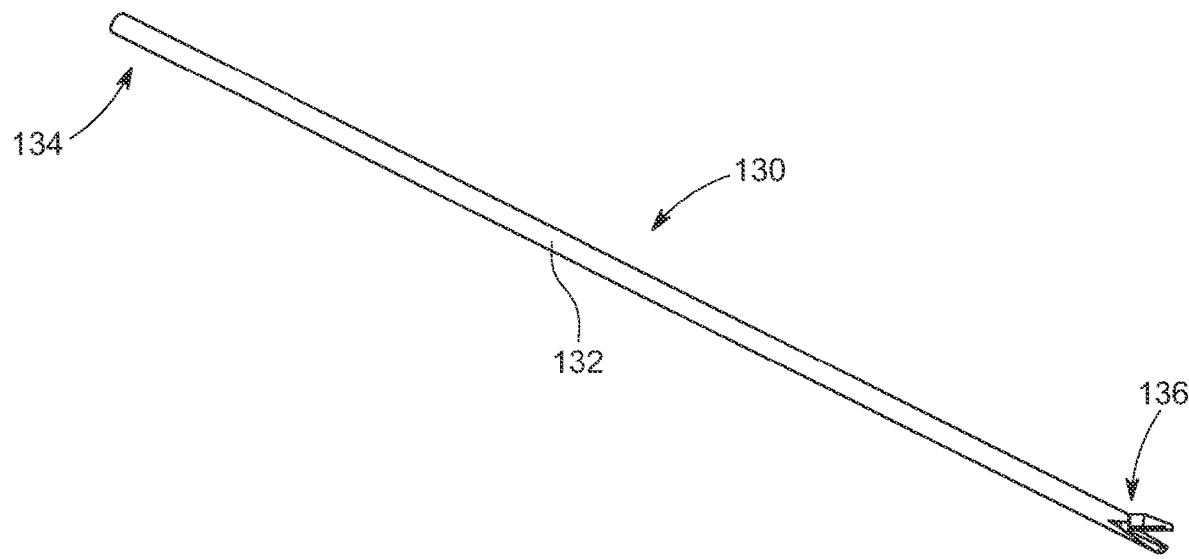
FIG. 8A is a perspective view of a needle driver used with the needle sheath of FIG. 1, in accordance with one embodiment of the present patent application.
Figure 8B:
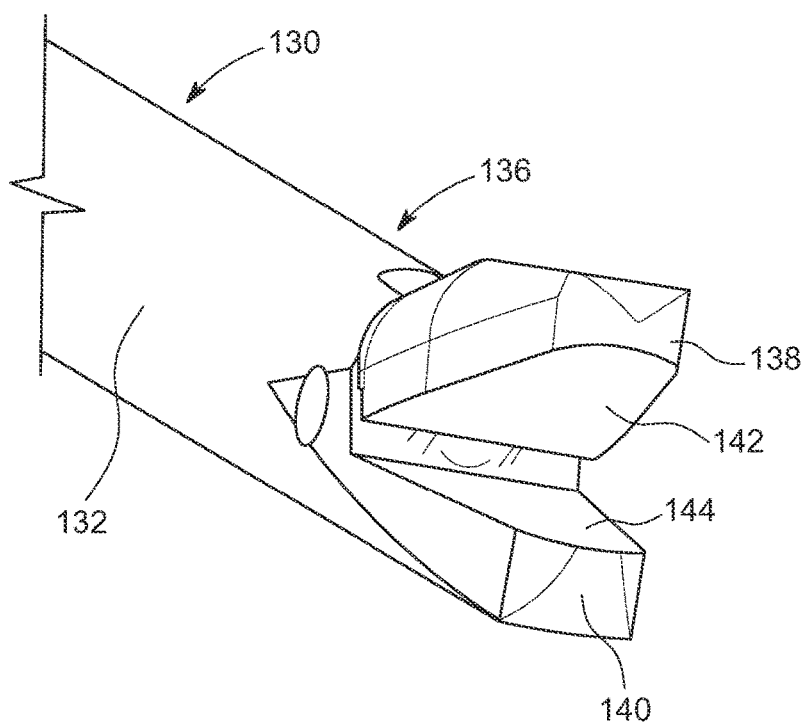
FIG. 8B is a magnified view of a distal end of the needle driver shown in FIG. 8A.

Referring to FIGS. 8A and 8B, in one embodiment, a needle driver 130 for securing the suture needle 118 (FIGS. 7A and 7B) preferably includes an elongated shaft 132 having a proximal end 134 and a distal end 136. In one embodiment, the needle driver 130 preferably has opposing first and second clamping jaws 138, 140 that are provided at the distal end 136 of the elongated shaft 132. In one embodiment, the first clamping jaw 138 preferably has a first clamping face 142 that opposes the second clamping jaw 140, and the second clamping jaw 140 preferably has a second clamping face 144 that opposes the first clamping jaw 138. The first and second clamping faces 142, 144 preferably oppose one another for applying a clamping force upon the distal tapered end of the suture needle. In one embodiment, the elongated shaft 132 of the needle driver 130 desirably has a cross-sectional diameter that is smaller than the inner diameter (ID) of the elongated conduit of the tubular shaft of the needle sheath so that the first and second clamping jaws 138, 140 at the distal end 136 of the needle driver 130 may be passed through the elongated conduit of the tubular shaft of the needle sheath for deploying a suture needle from the distal end of the needle sheath.

Figure 9:
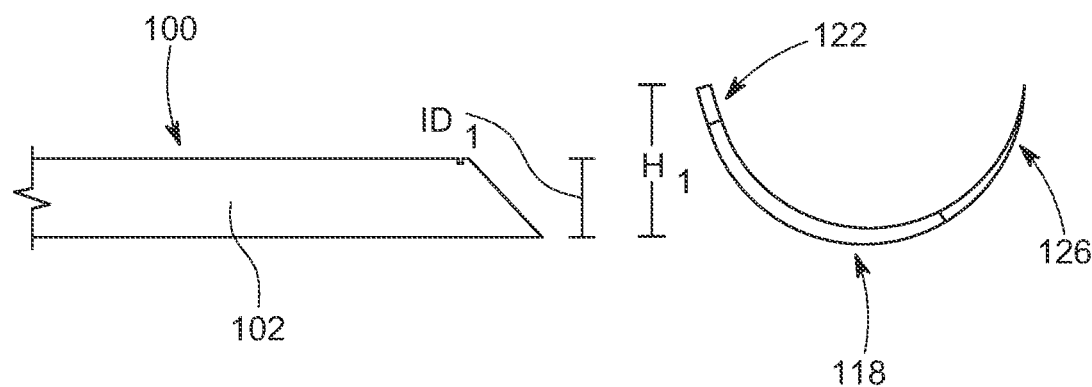
FIG. 9 is a side elevation view of the suture needle of FIG. 7A juxtaposed with the distal end of the needle sheath shown in FIG. 1.

Referring to FIG. 9, in one embodiment, the suture needle 118 may be made of a superelastic material for enabling the suture needle to be passed through the elongated conduit of the tubular shaft 102 of a needle sheath 100. In one embodiment, the suture needle 118 is curved between the proximal end 122 and the distal end 126 thereof. In one embodiment, in the normal, curved configuration, the suture needle 118 has a height $H_1$ that is greater than the inner diameter $ID_1$ of the elongated conduit of the tubular shaft 102 of the needle sheath 100.

Figure 10:
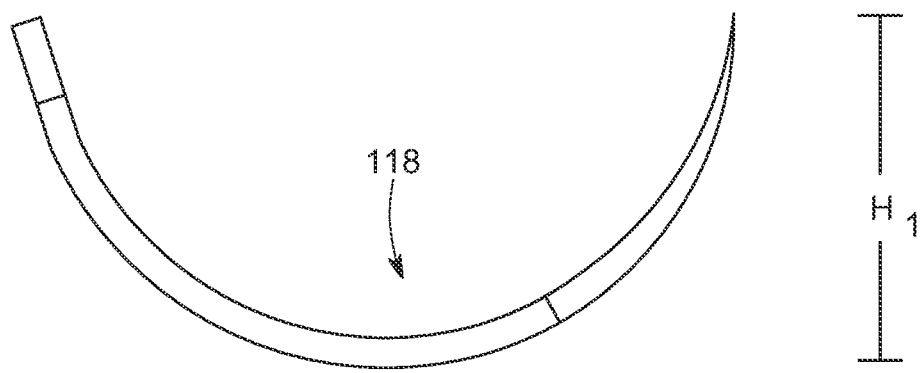
FIG. 10 is a magnified view of the suture needle shown in FIG. 9.
Figure 11:
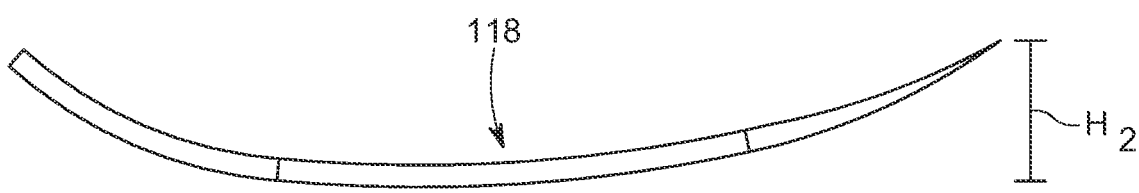
FIG. 11 is a side elevation view of the suture needle of FIG. 10 after the suture needle is transformed into a flattened configuration for passing through the needle sheath of FIG. 9, in accordance with one embodiment of the present patent application.

Referring to FIGS. 10 and 11, in one embodiment, the suture needle 118 is made of a superelastic material, which enables the suture needle to flex and/or transform from the normal, curved configuration shown in FIG. 10 to a flattened configuration shown in FIG. 11. In the configuration shown in FIG. 10, the suture needle 118 has a height $H_1$ that is greater than the inner diameter of the tubular shaft of the needle sheath. Referring to FIG. 11, in one embodiment, tension may be applied to the superelastic suture needle 118 to flatten and/or reduce the overall height of the suture needle so that it has a second height $H_2$ that is less than both the first height $H_1$ (FIG. 10) and the inner diameter $ID_1$ of the elongated conduit of the tubular shaft 102 of the needle sheath 100 (FIG. 9). As a result, the suture needle 118 is incapable of passing through the inner diameter $ID_1$ of the tubular shaft 102 of the needle sheath when in the normal, curved configuration of FIG. 10, but is able to be pass through the inner diameter $ID_1$ of the tubular shaft of the needle sheath when it is in the flattened configuration shown in FIG. 11. In one embodiment, after the suture needle has been passed through the needle sheath, the superelastic material of the suture needle preferably transforms the suture needle 118 back to its normal, curved configuration (FIG. 10) so that the suture needle may be used for a suturing procedure.

In one embodiment, the suture needle may repeatedly transform back and forth between the curved configuration shown in FIG. 10 and the flattened configuration shown in FIG. 11. As a result, the suture needle may be flattened a first time for advancing the suture needle through the tubular shaft of the needle sheath to locate the suture needle at a surgical site for use during a surgical procedure. At the surgical site, the superelastic properties of the suture needle enable the suture needle to transform back to its normal, curved configuration for use in a suturing procedure. At the conclusion of the surgical procedure, the suture needle may be placed under tension for flattening the suture needle for passing it through the smaller inner diameter of the elongated conduit of the tubular shaft of the needle sheath for removing the suture needle from the surgical site.

Figure 12:
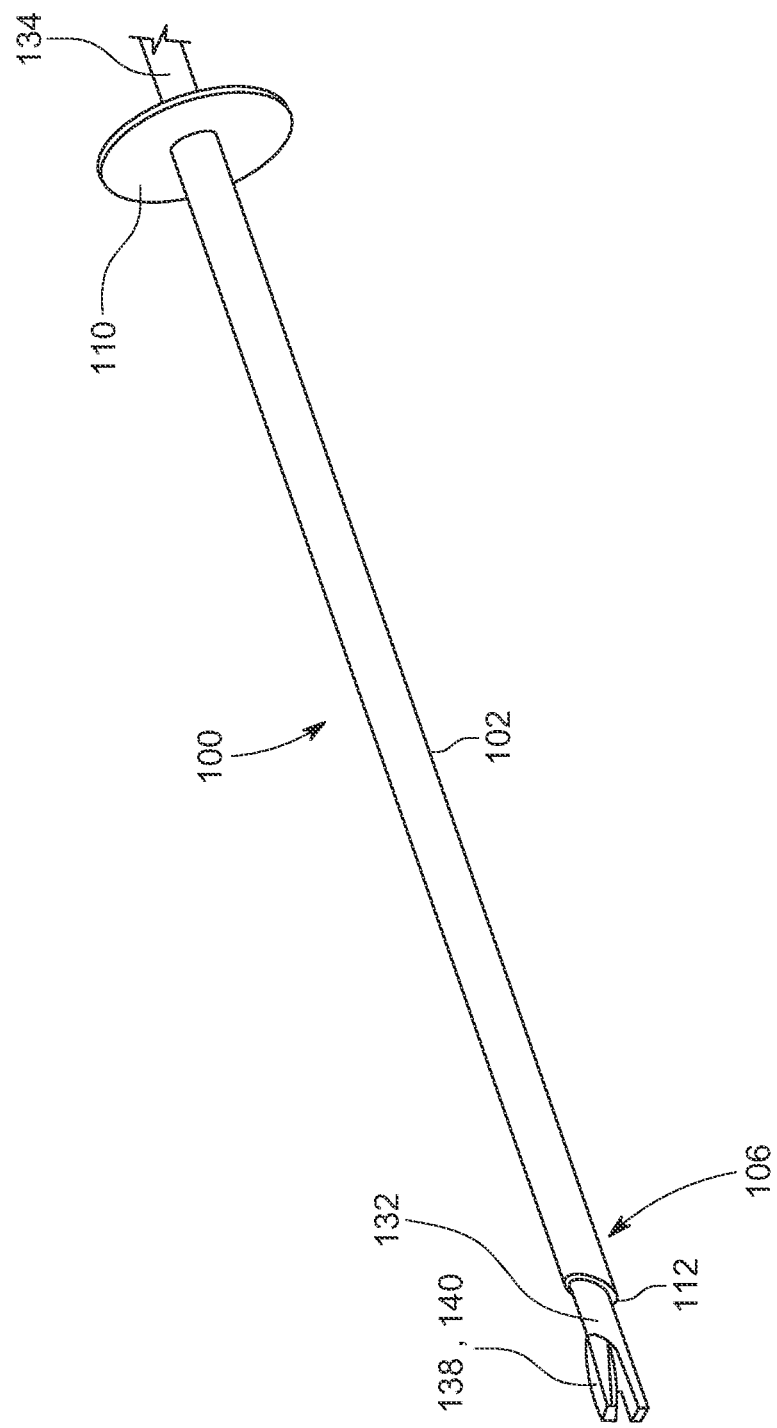
FIG. 12 is a perspective view of the needle sheath of FIG. 1 assembled with the needle driver of FIG. 8A, in accordance with one embodiment of the present patent application.

Referring to FIG. 12, in one embodiment, the tubular shaft 102 of the needle sheath 100 may be slid over the elongated shaft 132 of the needle driver 130 (FIG. 8A), whereby the first and second clamping jaws 138, 140 of the needle driver project beyond the chamfered edge 112 located at the distal end 106 of the tubular shaft 102 of the needle sheath 100. In one embodiment, the proximal end 134 of the elongated shaft 132 of the needle driver remains accessible at a location that is proximal to the flange 110 of the needle sheath 100 (e.g., outside a patient's body) for enabling surgical personnel to move the first and second clamping jaws 138, 140 relative to the distal end 106 of the tubular shaft 102 of the needle sheath 100.

Figure 13:
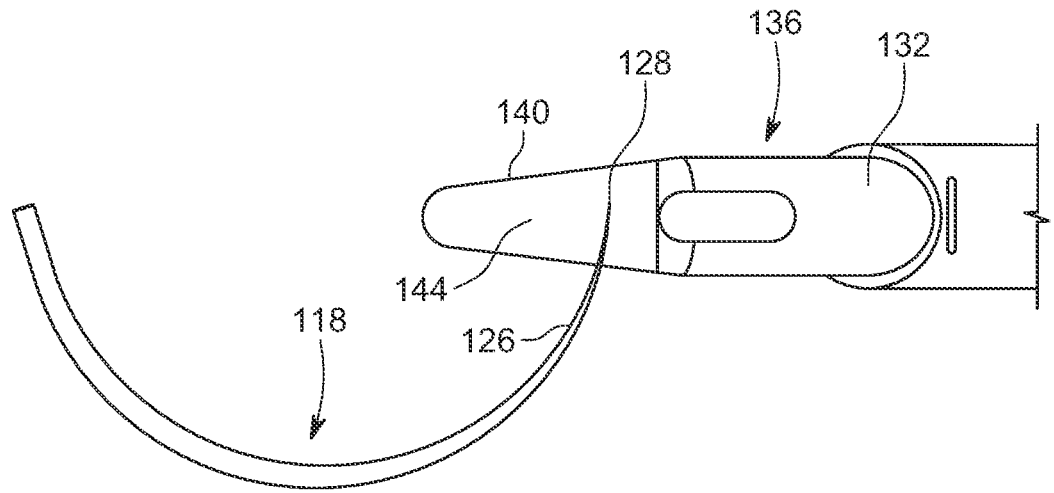
FIG. 13 shows a stage of a method of using a needle driver for securing a suture needle, in accordance with one embodiment of the present patent application.
Figure 14:
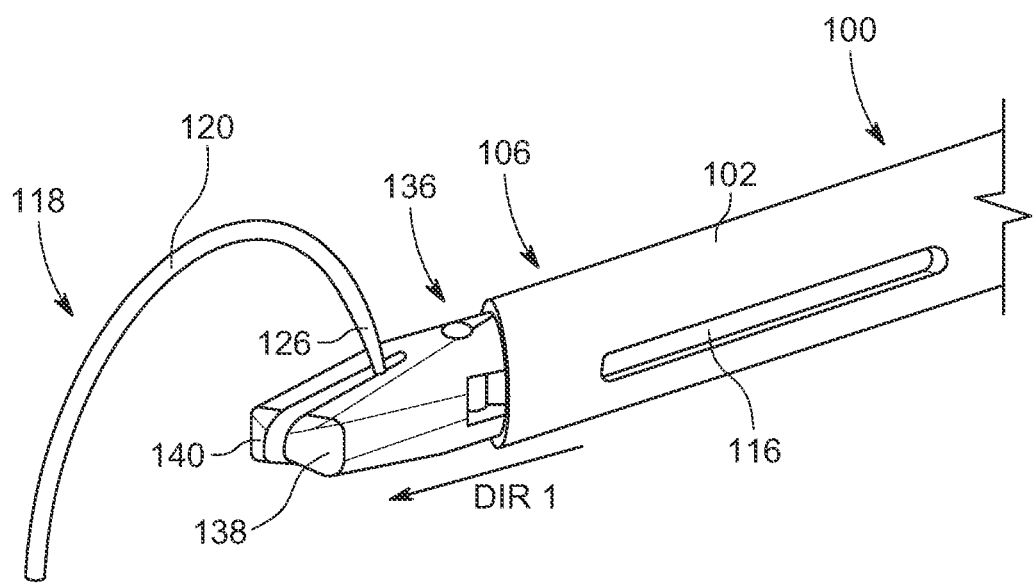
FIG. 14 shows a stage of a method of using the needle driver of FIG. 8A for retracting a suture needle into a distal end of a needle sheath, in accordance with one embodiment of the present patent application.

Referring to FIGS. 13 and 14, in one embodiment, the first and second clamping jaws 138, 140 located at the distal end 136 of the elongated shaft 132 of the needle driver are utilized for securing the tapered distal end 126 of the suture needle 118. In one embodiment, the clamping jaws preferably engage the tapered distal end 126 of the suture needle 118 so that the sharpened point 128 of the suture needle 118 is aligned over the second clamping surface 144 of the second clamping jaw 140 and the first clamping surface of the first clamping jaw. The outer perimeter of the second clamping surface 144 of the second clamping jaw 140 preferably surrounds the needle point 128 so that the point of the suture needle 118 is protected and surrounded by the first and second clamping jaws 138,140 of the needle driver, which prevents the sharpened point from being dulled, marred, and/or damaged as the suture needle is passed through the needle sheath.

In one embodiment, after the tapered distal end 126 of the suture needle 118 has been grasped between the first and second clamping jaws 138, 140, the distal end 106 of the tubular shaft 102 of the needle sheath 100 is preferably slid distally in the direction designated DIR1 for capturing the first and second clamping jaws 138, 140 and the secured suture needle 118 inside the distal end 106 of the needle sheath 100. In one embodiment, the tubular shaft 102 of the needle sheath 100 is slid over the suture needle 118 in an orientation that prevents the curved body portion 120 of the suture needle 118 from engaging with the needle relief slot 116 formed in the bottom side of the tubular shaft 102 of the needle sheath so that the suture needle 118 is completely captured within the elongated conduit 108 (FIG. 1) of the tubular shaft 102 of the needle sheath.

Figure 15A:
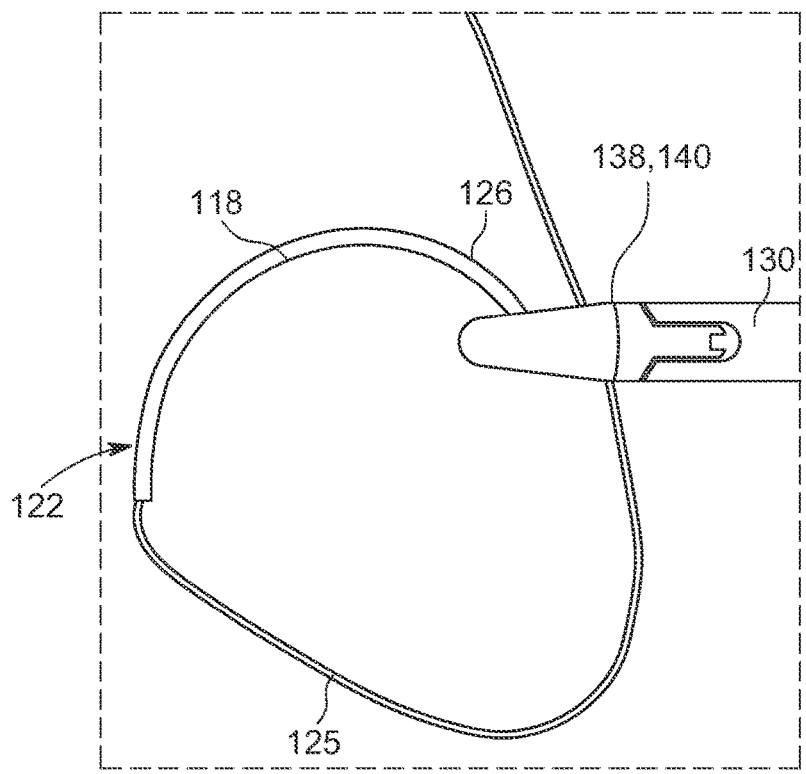
FIG. 15A shows a first stage of a method of loading a suture needle into a distal end of a needle sheath, in accordance with one embodiment of the present patent application.

Referring to FIG. 15A, in one embodiment, an armed suture needle preferably includes a suture needle 118 (e.g., a normally curved suture needle) and a suture thread 125 secured to the proximal end 122 of the suture needle. The suture thread 125 is preferably flexible and may be utilized for closing a wound at a surgical site. In one embodiment, the tapered distal end 126 of the suture needle 118 is secured between the first and second clamping jaws 138, 140 of a needle driver 130 with the sharpened point 128 (FIG. 13) of the suture needle located between the first and second clamping jaws 138, 140 and protected by the outer perimeters of the clamping jaws. In one embodiment, a section of the suture thread 125 may also be secured between the first and second clamping jaws 138, 140 so that both the needle point 128 (FIG. 7A) of the suture needle 118 and the suture thread 125 are held between the opposing jaws. Clamping onto both the suture needle and the suture thread may facilitate passing the armed suture needle through the needle sheath.

Figure 15B:
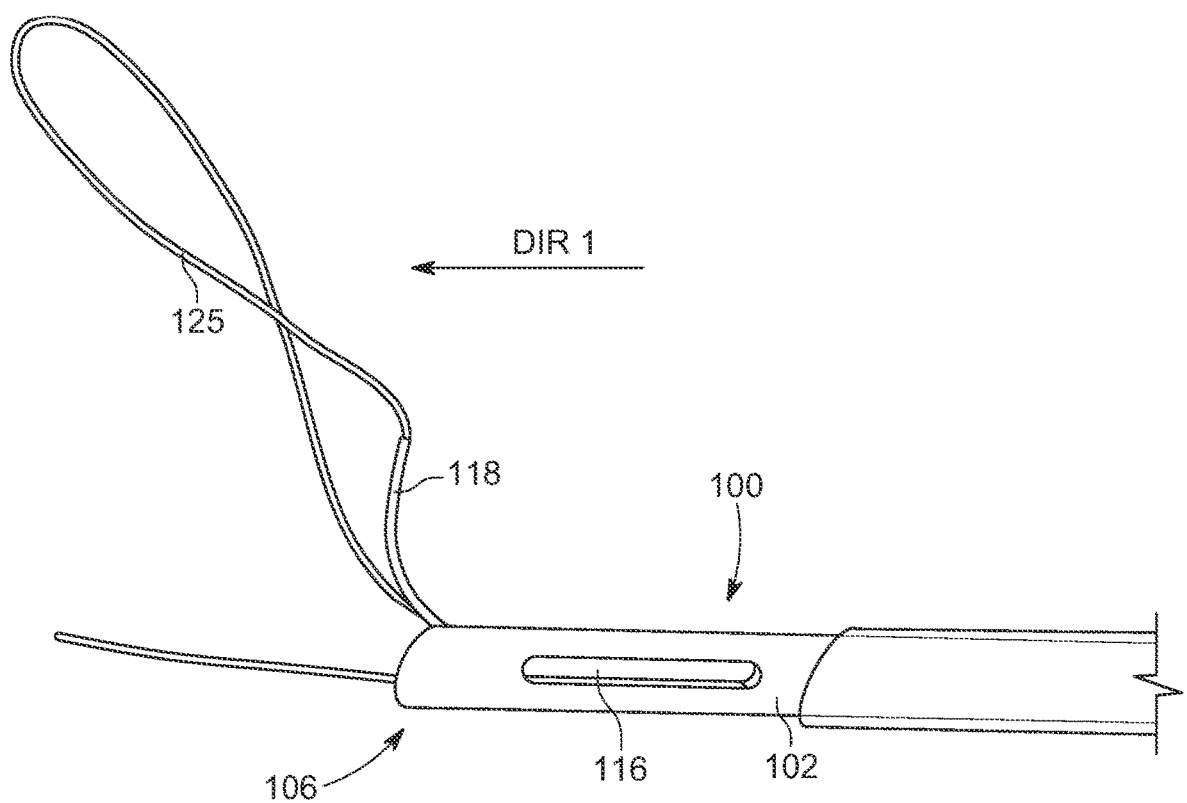
FIG. 15B shows a second stage of a method of loading a suture needle into a distal end of a needle sheath, in accordance with one embodiment of the present patent application.

Referring to FIG. 15B, in one embodiment, after the first and second clamping jaws of the needle driver have secured the suture needle 118 and the suture thread 125, the distal end 106 of the tubular shaft 102 of the needle sheath 100 is preferably slid in the distal direction designated DIR1 so that the suture needle 118 including the needle point is completely captured within the elongated conduit of the tubular shaft 102 of the needle sheath 100. As the curved suture needle is pulled into the distal end of the needle sheath 100, the suture needle 118 preferably transforms from a curved configuration to a flattened configuration for fitting inside elongated conduit of the needle sheath. In one embodiment, the tubular shaft 102 of the needle sheath is oriented relative to the suture needle 118 so that no portion of the suture needle 118 engages or passes through the needle relief slot 116 formed in the bottom side of the tubular shaft 102. As the suture needle 118 is captured by the advancing tubular shaft 102 of the needle sheath 100, the suture needle 118 preferably flattens to the configuration shown in FIG. 11 so that it may fit within the inner diameter of the elongated conduit of the tubular shaft 102.

Figure 16A:
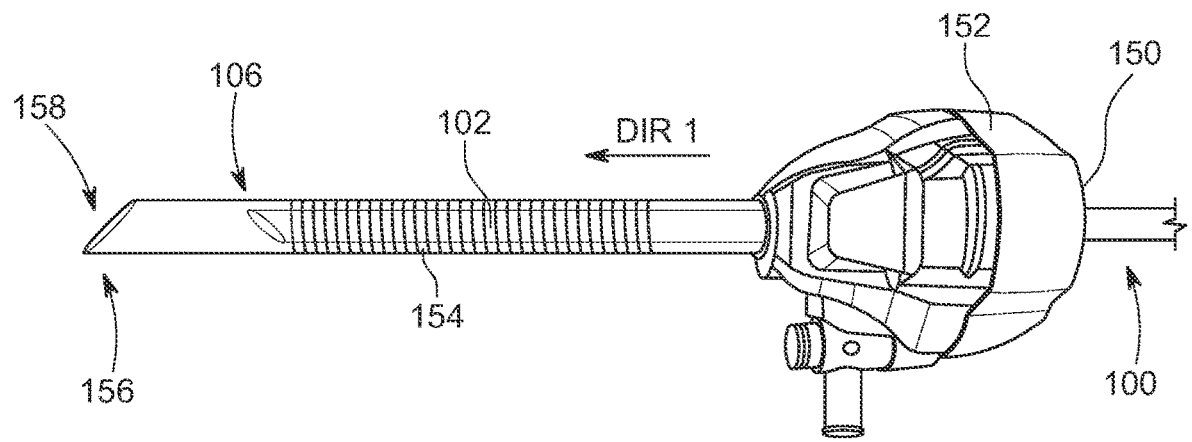
FIG. 16A shows a first stage of a method of using a needle sheath for delivering a suture needle to a surgical site, in accordance with one embodiment of the present patent application.
Figure 16B:
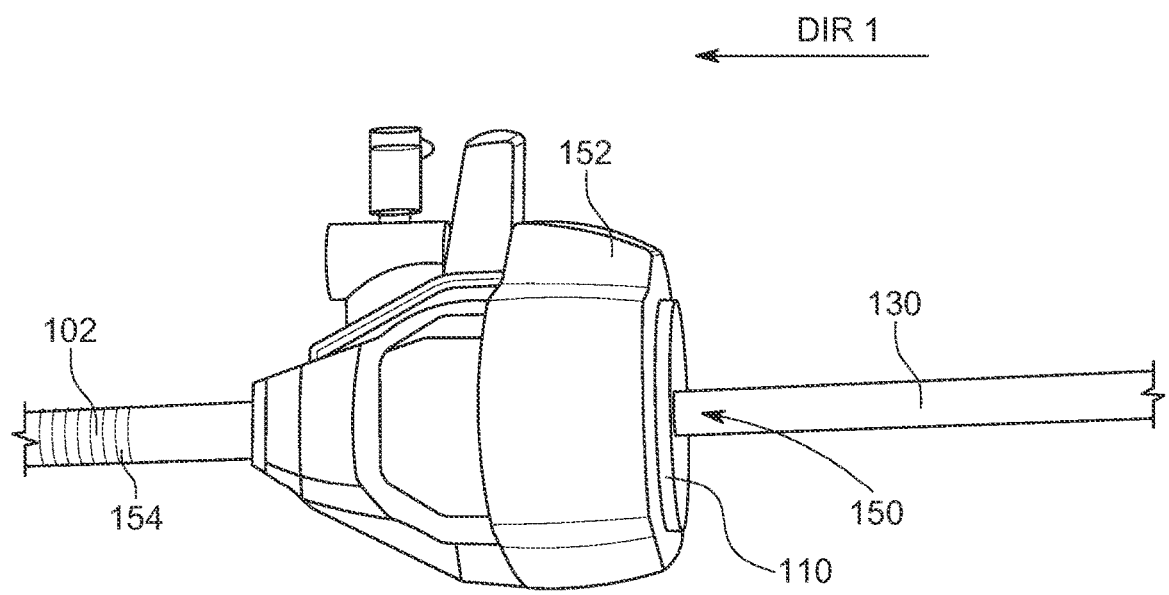
FIG. 16B shows a second stage of a method of using a needle sheath for delivering a suture needle to a surgical site, in accordance with one embodiment of the present patent application.

Referring to FIGS. 16A and 16B, in one embodiment, after the suture needle 118 and suture thread 125 (FIG. 15B) have been captured inside the tubular shaft 102 of the needle sheath 100, the distal end 106 of the needle sheath is desirably passed through an opening at a proximal end 150 of a trocar 152. In one embodiment, the trocar 152 preferably has an elongated lumen 154 with a distal end 156 having a distal opening 158 that is located at a surgical site inside a patient. In one embodiment, the tubular shaft 102 of the needle sheath 100 is preferably passed through the lumen 154 of the trocar 152 in a distal direction designated DIR1 until the stop flange 110 abuts against the proximal end 150 of the trocar 152 for halting distal movement of the needle sheath.

Figure 16C:
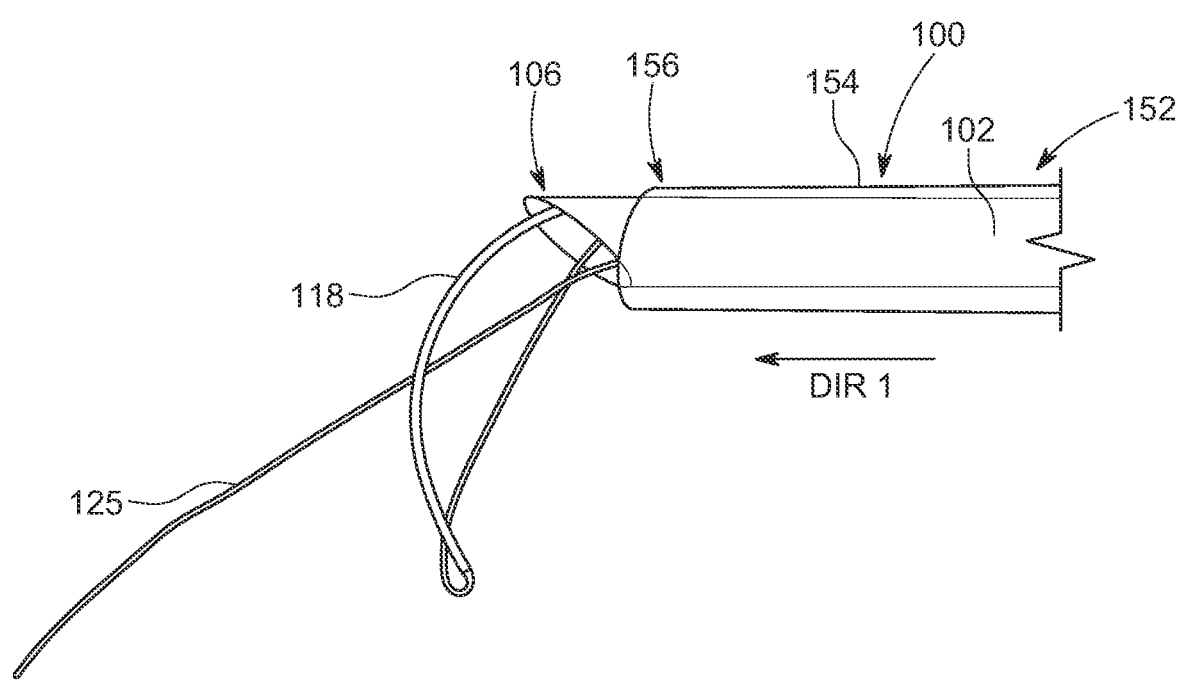
FIG. 16C shows a third stage of a method of using a needle sheath for delivering a suture needle to a surgical site, in accordance with one embodiment of the present patent application.

Referring to FIG. 16C, in one embodiment, the distal end 106 of the tubular shaft 102 of the needle sheath 100 is preferably advanced in the distal direction DIR1 beyond the distal end 156 of the lumen 154 of the trocar 152.

Figure 16D:
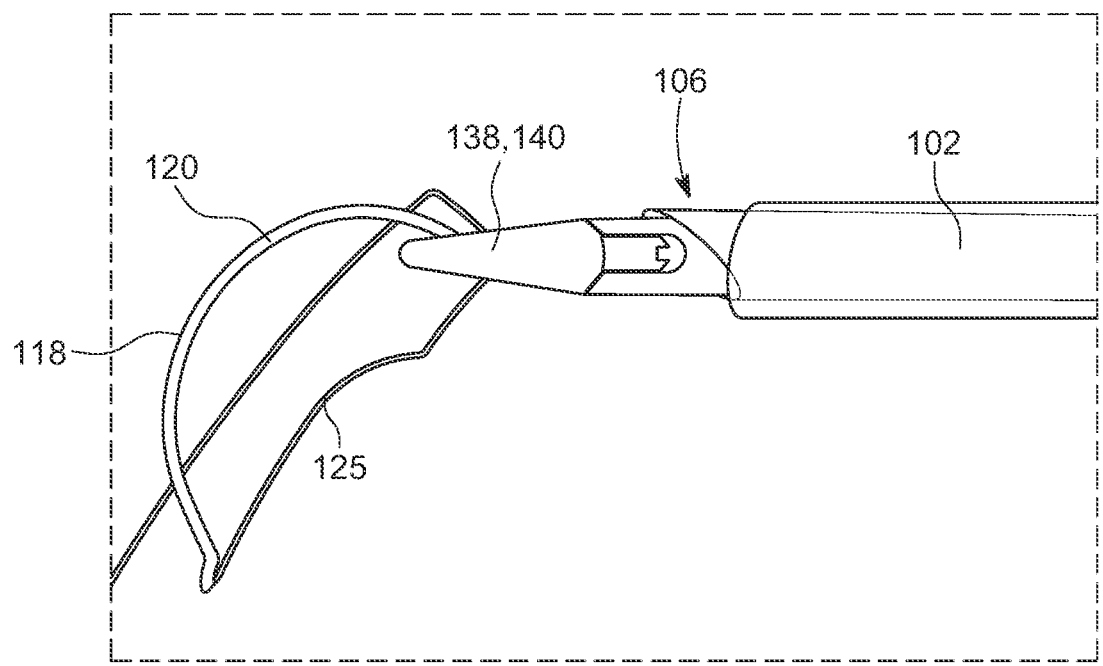
FIG. 16D shows a fourth stage of a method of using a needle sheath for delivering a suture needle to a surgical site, in accordance with one embodiment of the present patent application.

FIG. 16D shows the suture needle 118 and the flexible suture thread 125 after the first and second clamping jaws 138, 140 of the needle driver have advanced the suture needle 118 and the suture thread 125 beyond the distal end 106 of the tubular shaft 102 of the needle sheath. After the suture needle 118 has been advanced beyond the distal end 106 of the tubular shaft 102 of the needle sheath, the suture needle 118 made of elastic or superelastic materials transforms back to its normal, curved configuration. The suture needle 118 and the suture thread 125 have now been delivered to a surgical site whereby the components may be utilized during a suturing operation for closing a wound or a surgical opening at the surgical site.

Figure 17A:
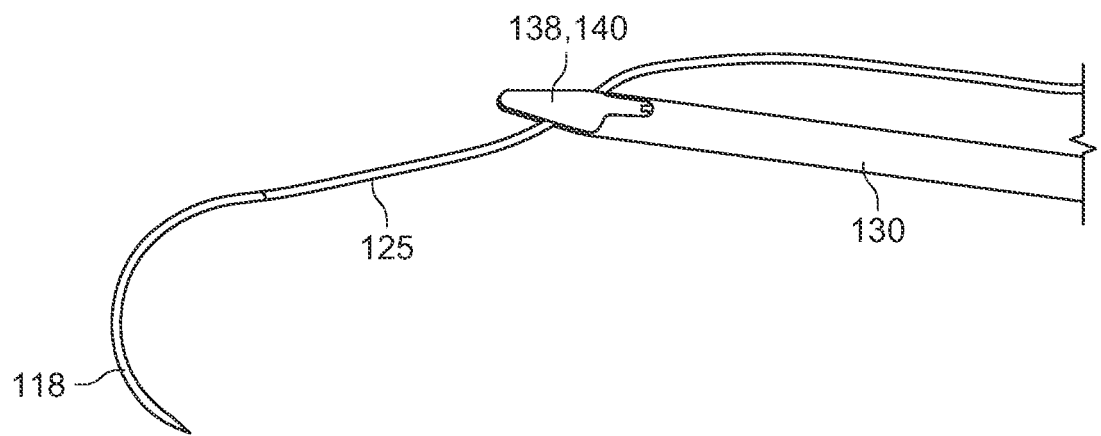
FIG. 17A shows a first stage of a method of using a needle sheath for removing a suture needle from a surgical site, in accordance with one embodiment of the present patent application.

Referring to FIG. 17A, in one embodiment, at the conclusion of a surgical procedure, the suture needle 118 and the flexible suture thread material 125 may be removed from the surgical site by withdrawing the components through the needle sheath. In one embodiment, the first and second clamping jaws 138, 140 at the distal end of the needle driver 130 may be closed for securing the flexible suture thread 125 between the clamping jaws.

Figure 17B:
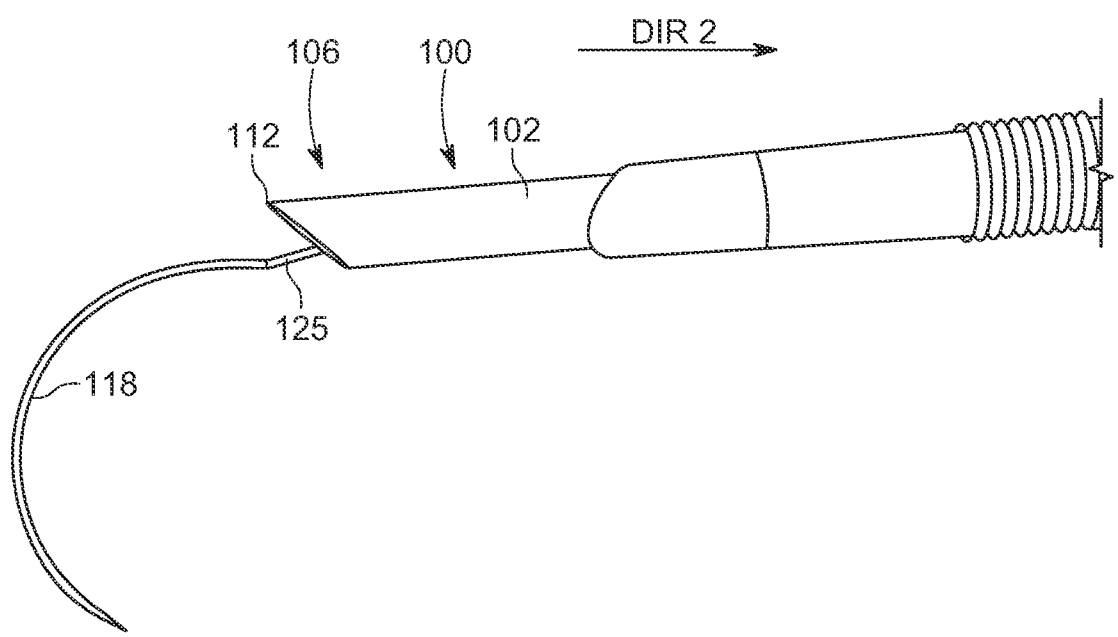
FIG. 17B shows a second stage of a method of using a needle sheath for removing a suture needle from a surgical site, in accordance with one embodiment of the present patent application.

Referring to FIG. 17B, in one embodiment, the needle driver may then be withdrawn through the needle sheath 100 in a proximal direction designated DIR2 for pulling the suture thread 125 and the attached suture needle 118 into the distal end 106 of the tubular shaft 102 of the needle sheath 100. In one embodiment, as the needle is pulled into the distal end of the tubular shaft 102 of the needle sheath 100, the chamfered edge 112 at the distal end 106 of the tubular shaft 102 preferably engages the body of the suture needle to orient the suture needle 118 relative to the tubular shaft 102. In one embodiment, the chamfered edge orients the suture needle so that the cured body of the suture needle is aligned with the suture relief slot 116 (FIGS. 3A-3C) located at the bottom side of the tubular shaft of the needle sheath.

FIGS. 18A-18F show a schematic view of the suture needle 118 being pulled into the distal end 106 of the tubular shaft 102 of the needle sheath 100, whereupon the chamfered edge 112 orients the curved suture needle so that the suture needle is aligned with the needle relief slot 116 formed in the bottom side of the tubular shaft 102 of the needle sheath 100. For clarity, the suture thread 125 (FIG. 17A) secured to the proximal end of the suture needle 118 is not shown.

Figure 18A:
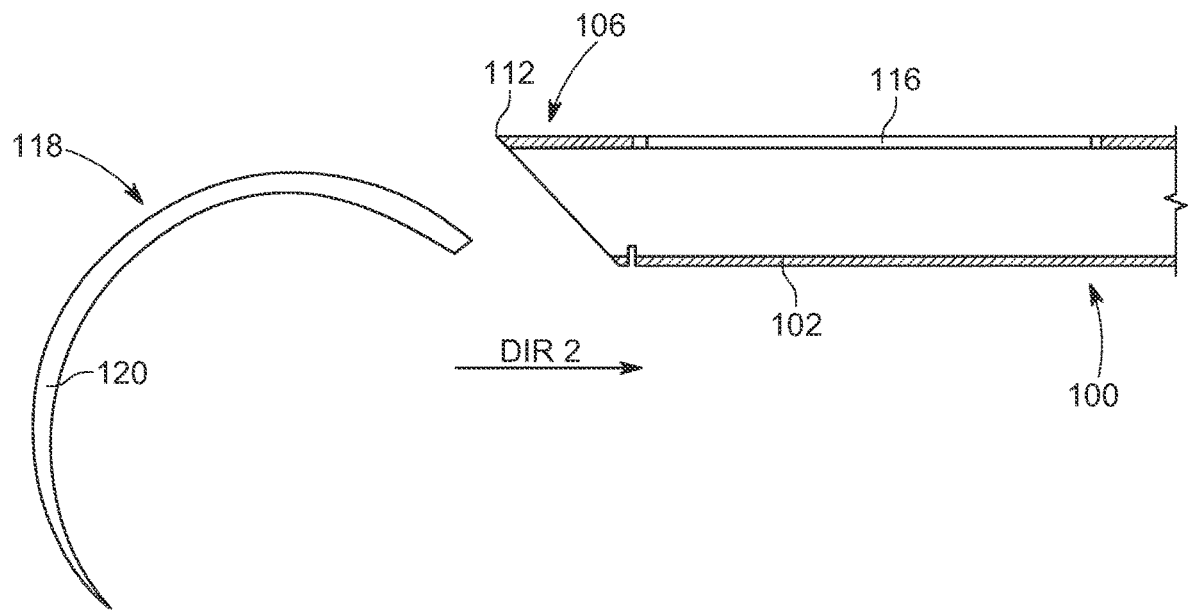
FIG. 18A shows a first stage of a method of withdrawing a suture needle into a distal end of a needle sheath, in accordance with one embodiment of the present patent application.
Figure 18B:
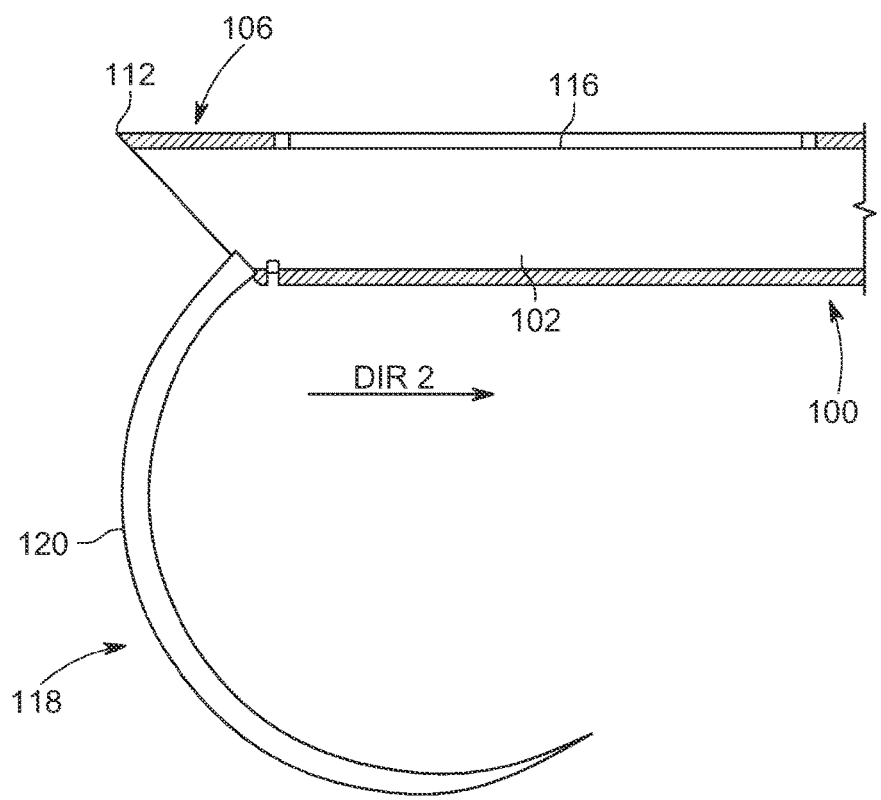
FIG. 18B shows a second stage of a method of withdrawing a suture needle into a distal end of a needle sheath, in accordance with one embodiment of the present patent application.

Referring to FIGS. 18A-18B, as the suture needle 118 (attached to the suture thread, which is secured by the clamping jaws of the needle driver) is pulled in a proximal direction designated DIR2 into the distal end 106 of the tubular shaft 102, the chamfered edge 112 located at the bottom side of the tubular shaft 102 preferably orients the curved body portion 120 of the suture needle 118 so that the curved body portion 120 moves into alignment with the needle relief slot 116 formed in the bottom side of the tubular shaft 102. During removal from the surgical site, the suture needle 118 is oriented so that the needle point 128 of the suture needle 118 trails the proximal end 122 of the suture needle.

Figure 18C:
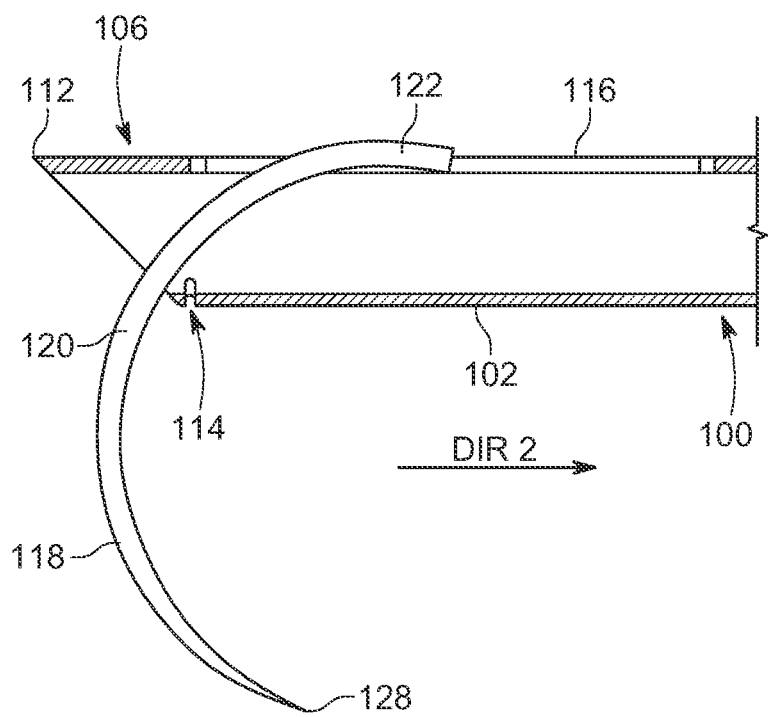
FIG. 18C shows a third stage of a method of withdrawing a suture needle into a distal end of a needle sheath, in accordance with one embodiment of the present patent application.
Figure 18D:
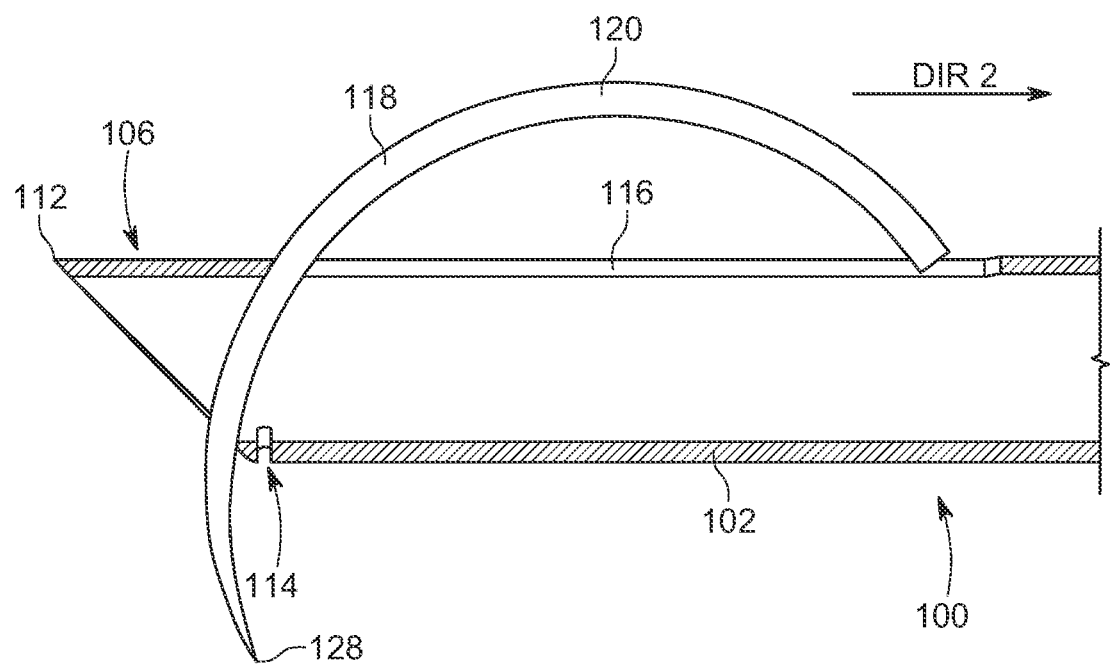
FIG. 18D shows a fourth stage of a method of withdrawing a suture needle into a distal end of a needle sheath, in accordance with one embodiment of the present patent application.
Figure 18E:
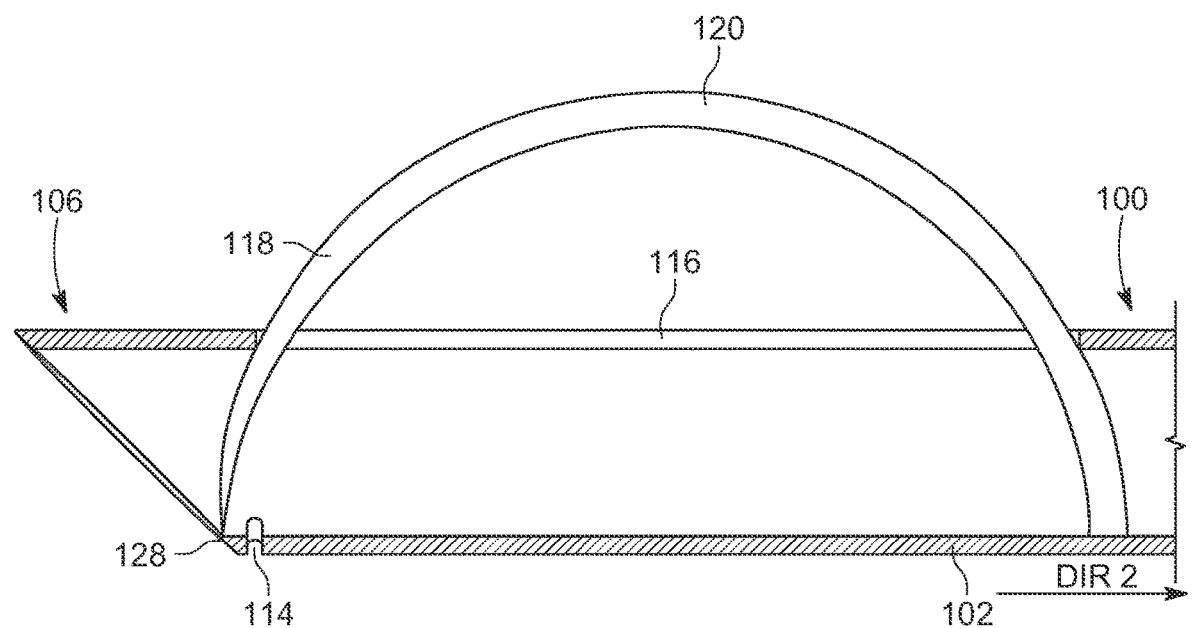
FIG. 18E shows a fifth stage of a method of withdrawing a suture needle into a distal end of a needle sheath, in accordance with one embodiment of the present patent application.

Referring to FIGS. 18C-18E, further retraction of the suture needle 118 into the distal end 106 of the tubular shaft 102 further orients the suture needle 118 so that the curved body 120 of the suture needle advances into the needle relief slot 116 formed in the bottom side of the tubular shaft 102 and so that the point 128 of the suture needle 118 is brought into alignment with the needle point slot 114 formed in the top side tubular shaft 102. The needle relief slot 116 of the tubular shaft 102 of the needle sheath 100 preferably enables the suture needle 118 to be pulled into the distal end of the tubular shaft with the suture needle in its normal, curved shape, with minimal tension being applied to the curved body of the suture needle, and with minimal distortion of the curved shape of the suture needle.

Figure 18F:
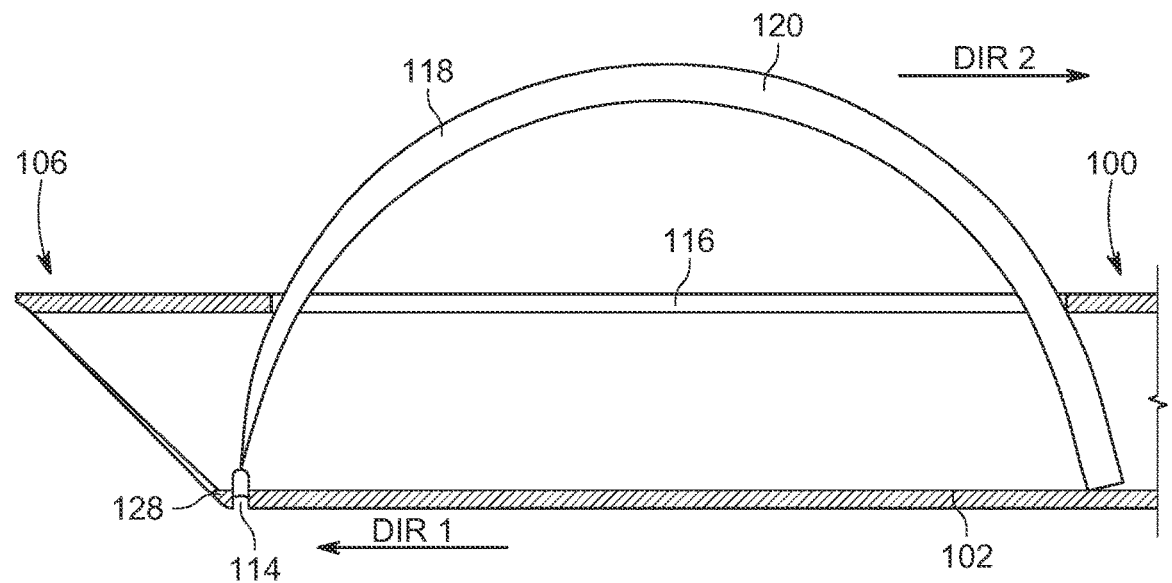
FIG. 18F shows a sixth stage of a method of withdrawing a suture needle into a distal end of a needle sheath, in accordance with one embodiment of the present patent application.

Referring to FIG. 18F, during further removal of the suture needle 118 in the proximal direction designated DIR2, the suture needle 118 is fully captured by the distal end of the tubular shaft 102 of the needle sheath 100, with the curved body portion 120 of the suture needle passing through the needle relief slot 116 and the sharpened point 128 of the suture needle captured within the needle point slot 114. In the stage of the withdrawal procedure shown in FIG. 18F, the suture needle 118 is preferably in its normal, curved configuration, a portion of the suture needle extends though the needle relief slot 116 for being located outside the tubular shaft of the needle sheath, and the suture needle is not being subjected to external forces such as compression or tension. In one embodiment, capturing the needle point 128 of the suture needle 118 within the needle point slot 114 serves to prevent the suture needle from moving distally in the direction designated DIR1 (i.e., back into the surgical site), such as when tension is applied to the suture needle.

In one embodiment, the needle point slot 114 may be formed entirely through the full thickness of the wall of the tubular shaft 102, or may simply be a recess or depression formed in the inner surface of the wall of the tubular shaft 102 that captures the needle point. In one embodiment, the length of the needle relief slot 116 and its relative axial location with respect to the needle point slot 114 may match the geometry of the suture needle 118 that is passed through the tubular shaft 102 of the needle sheath 100. Thus, the length of the needle relief slot 116 and its axial location with respect to the needle point slot 114 may be a function of the needle curvature (i.e., the degree of curvature and the radius of curvature) and the inner diameter $ID_1$ of the tubular shaft 102 of the needle sheath 100.

Figure 19A:
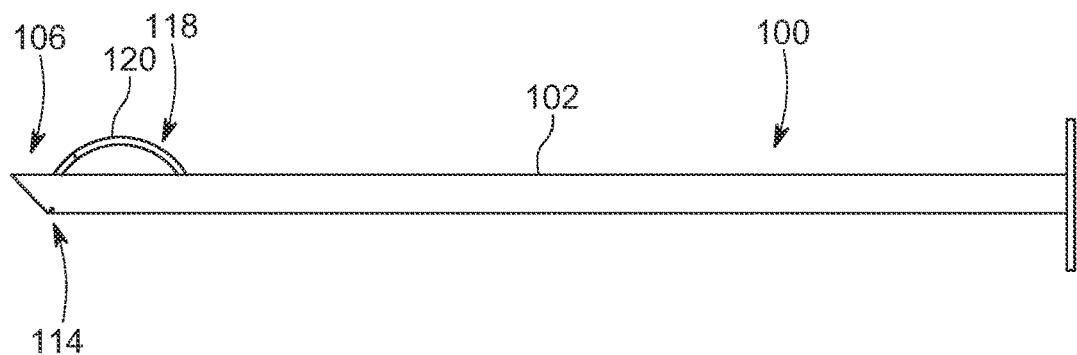
FIG. 19A is a side elevation view of the suture needle and needle sheath shown in FIG. 18F.
Figure 19B:
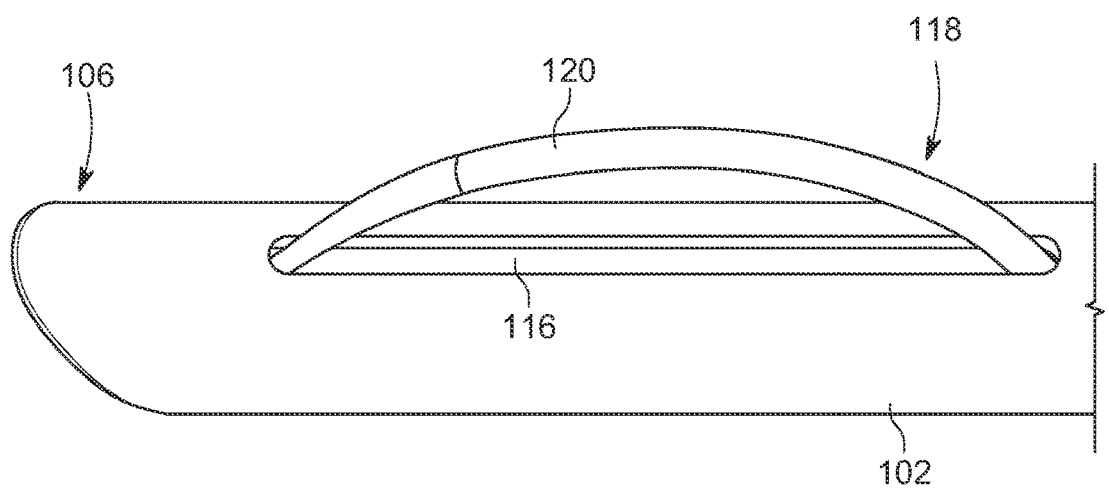
FIG. 19B is a bottom view of a distal end of the needle sheath and the suture needle shown in FIG. 18F.
Figures 19C, 19D:
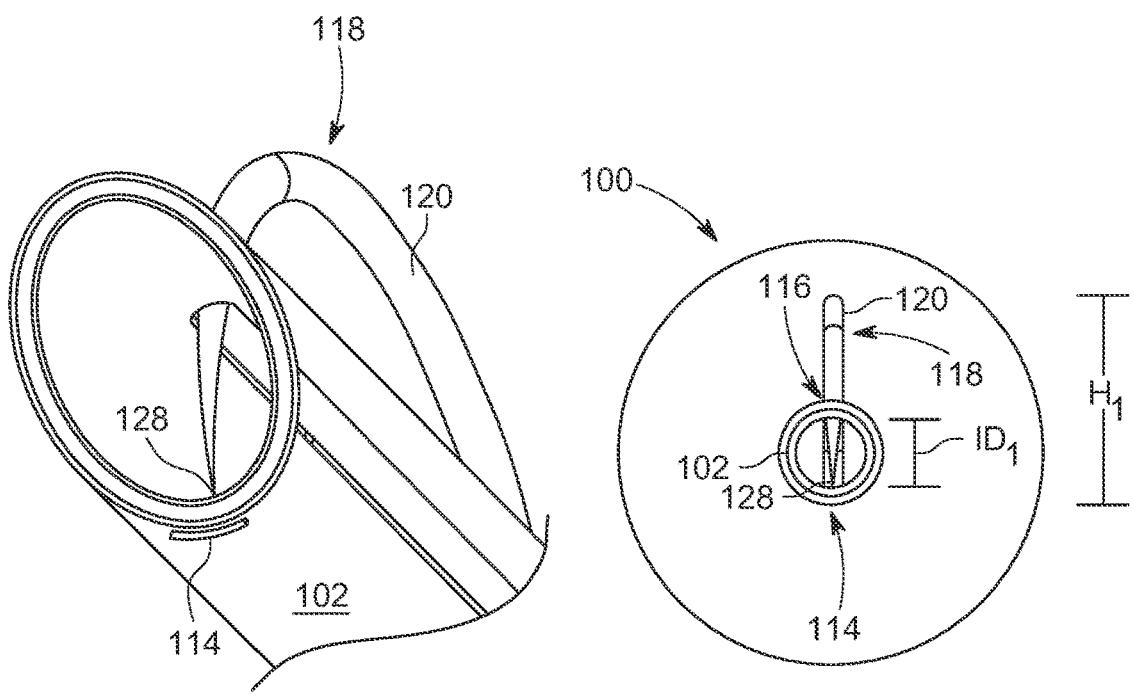
FIG. 19C is a perspective view of a distal end of the needle sheath and the suture needle shown in FIG. 18F.
FIG. 19D is a distal end view of the needle sheath and the suture needle shown in FIG. 19A.

Referring to FIGS. 19A-19D, when the suture needle 118 has been pulled into the distal end 106 of the tubular shaft 102 of the needle sheath 100 to the location shown in FIG. 18F, the curved body portion 120 of the suture needle 118 passes through the needle relief slot 116 of the needle sheath so that it is located outside the tubular shaft 102. The sharpened point 128 of the suture needle 118 is captured within the needle point slot 114. Referring to FIG. 19D, at this stage of removal of the suture needle 118, the suture needle 118 is curved and has a height H1 that is greater than the inner diameter ID1 of the tubular shaft 102 of the needle sheath 100.

Figure 20:
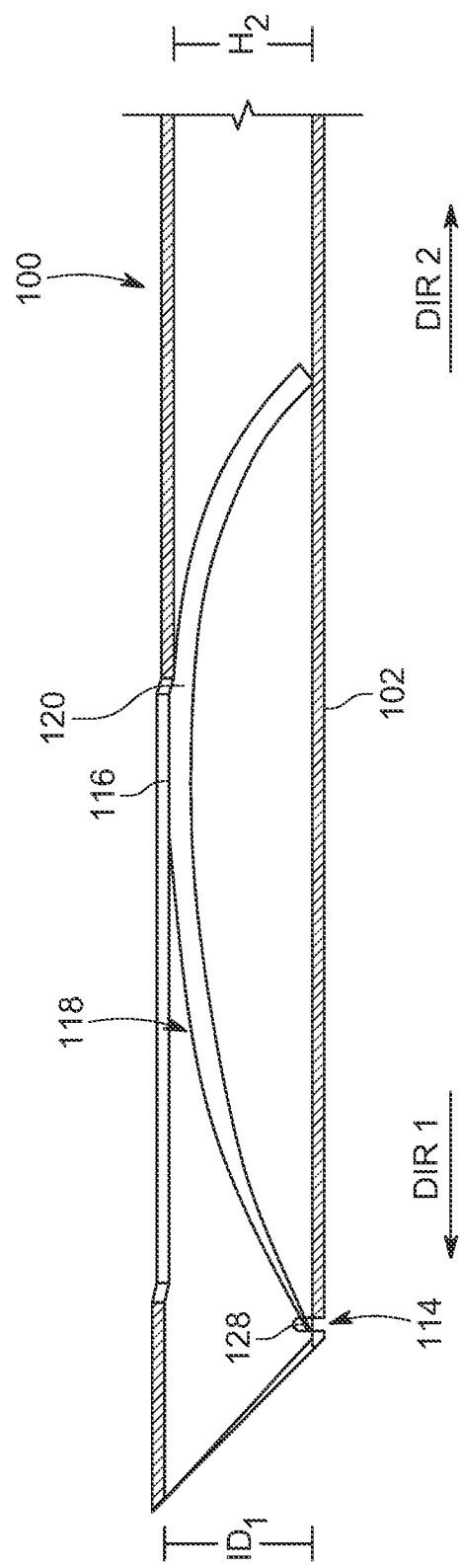
FIG. 20 is a cross-sectional view of a distal end of a needle sheath with a suture needle under tension and in a flattened configuration for passing through an elongated conduit of the needle sheath, in accordance with on embodiment of the present patent application.

Referring to FIG. 20, in one embodiment, after the stage of the suture needle removal process shown in FIGS. 18F and 19A-19D, as the needle driver continues to pull the suture thread and the suture needle 118 in the proximal direction DIR2 toward the proximal end of the tubular shaft 102 of the needle sheath 100, the suture needle 118 flexes into a flatter configuration (e.g., from curved to less curved) for being completely positioned inside the inner diameter $ID_1$ of the tubular shaft 102 of the needle sheath 100. In the flattened or flatter configuration shown in FIG. 20, the curved elongated body 120 of the needle 118 no longer extends through the needle relief slot 116 formed in the bottom side of the tubular shaft 102. In one embodiment, the flattened suture needle 118 defines a height $H_2$ that is less than or equal to the inner diameter $ID_1$ of the tubular shaft 102 of the needle sheath 100. In the flattened configuration shown in FIG. 20, the suture needle 118 may be retracted through the tubular shaft 102 in the proximal direction DIR2 for being removed from the proximal end of the trocar 152 (FIG. 16B). As tension is applied to the suture needle 118 via the suture thread being pulled by the needle driver, the needle point slot 114 preferably engages the sharpened point 128 of the suture needle 118 to prevent the suture needle from moving in the distal direction DIR1. For example, if a suture thread under tension became detached from the proximal end of the suture needle, the needle point slot would preferably function as a catch and/or stop to prevent the suture needle under tension from springing out of the distal end of the tubular sheath and back into the surgical site where it could damage tissue.

Figure 21:
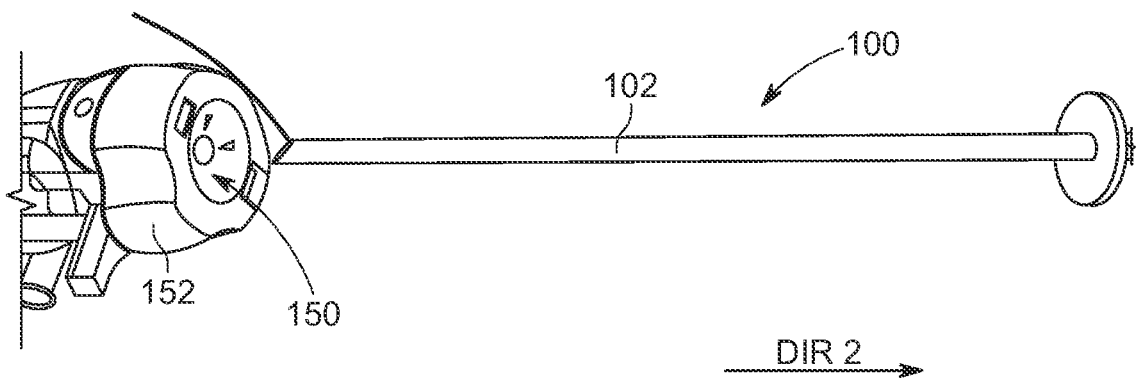
FIG. 21 shows a method of retracting a needle sheath from a proximal end of a trocar, in accordance with one embodiment of the present patent application.

Referring to FIG. 21, after the suture needle 118 has been fully retracted into the tubular shaft 102 of the needle sheath 100, the tubular shaft 102 may be withdrawn in the proximal direction designated DIR2 for removing the needle sheath from the opening at the proximal end 150 of the trocar 152.

Figure 22:
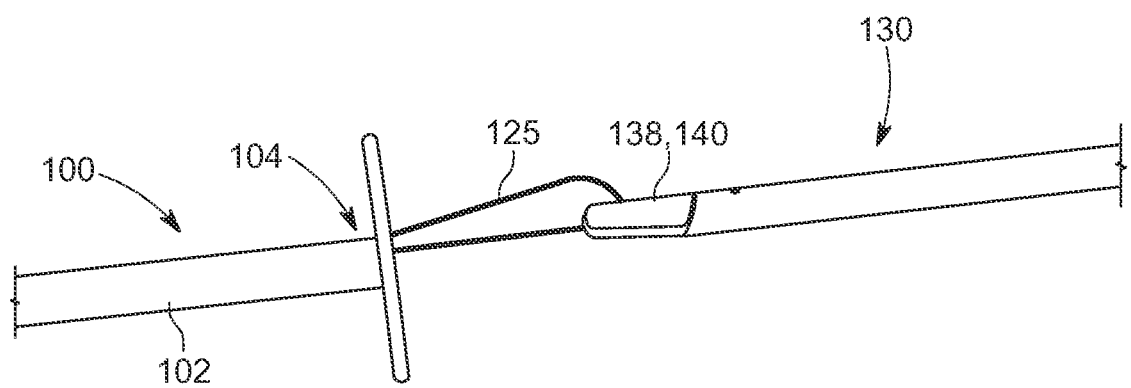
FIG. 22 shows a first stage of a method of using a needle driver for removing a suture thread and a suture needle from a proximal end of a needle sheath, in accordance with one embodiment of the present patent application.

Referring to FIG. 22, after the needle sheath 100 has been withdrawn from the proximal end of the trocar, the clamping jaws 138, 140 at the distal end of the needle driver 130 may be used to pull the flexible suture thread 125 from a proximal opening of the needle sheath 100.

Figure 23:
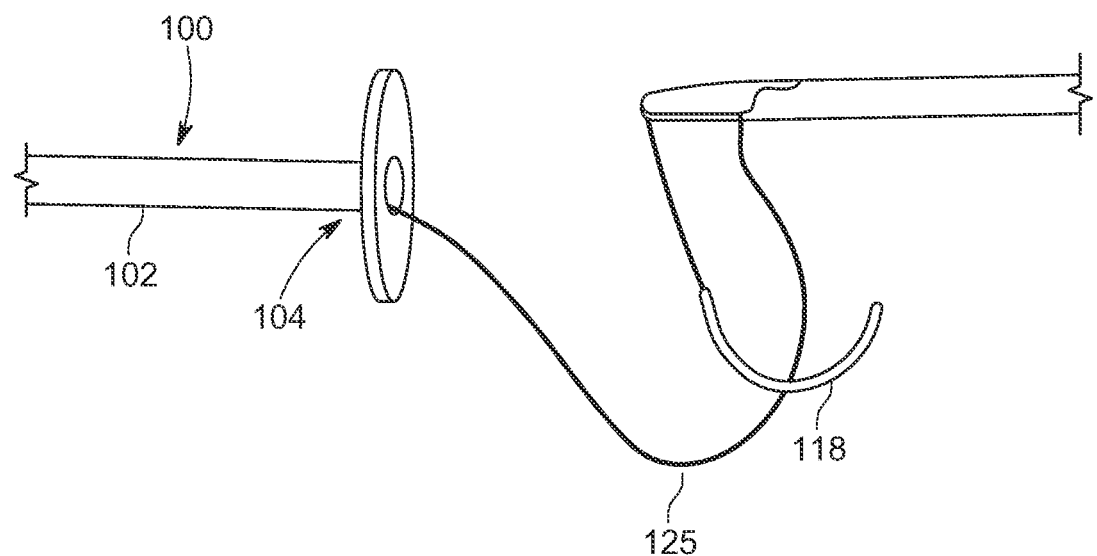
FIG. 23 shows a second stage of a method of using a needle driver for removing a suture thread and a suture needle from a proximal end of a needle sheath, in accordance with one embodiment of the present patent application.

FIG. 23 shows further extraction of the flexible suture thread 125 and the suture needle 118 (secured to the suture thread) from the proximal end 104 of the tubular sheath 102 of the needle sheath 100.

Figure 24:
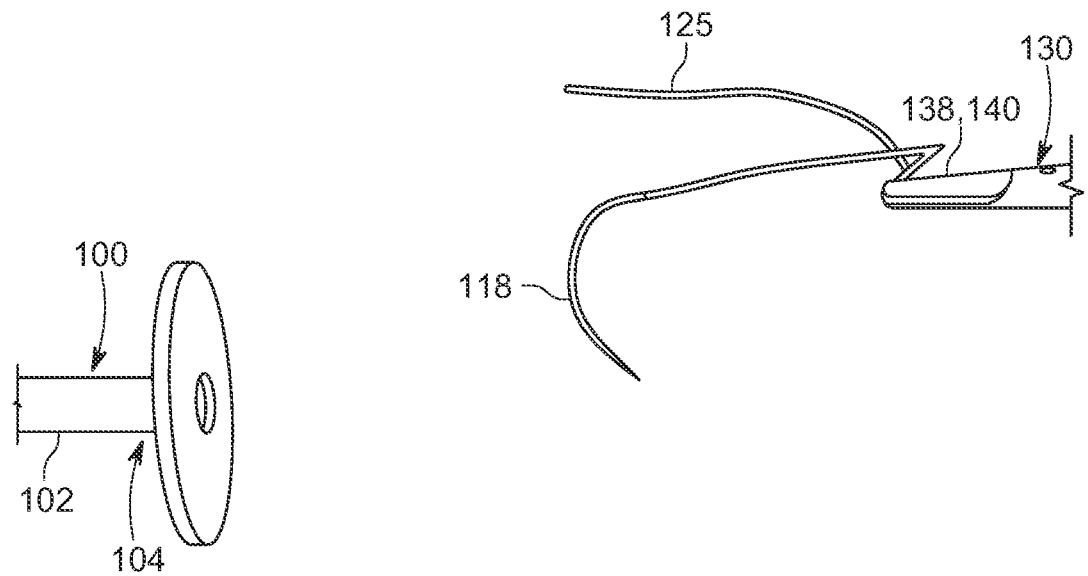
FIG. 24 shows a third stage of a method of using a needle driver for removing a suture thread and a suture needle from a proximal end of a needle sheath, in accordance with one embodiment of the present patent application.
Figure 25:
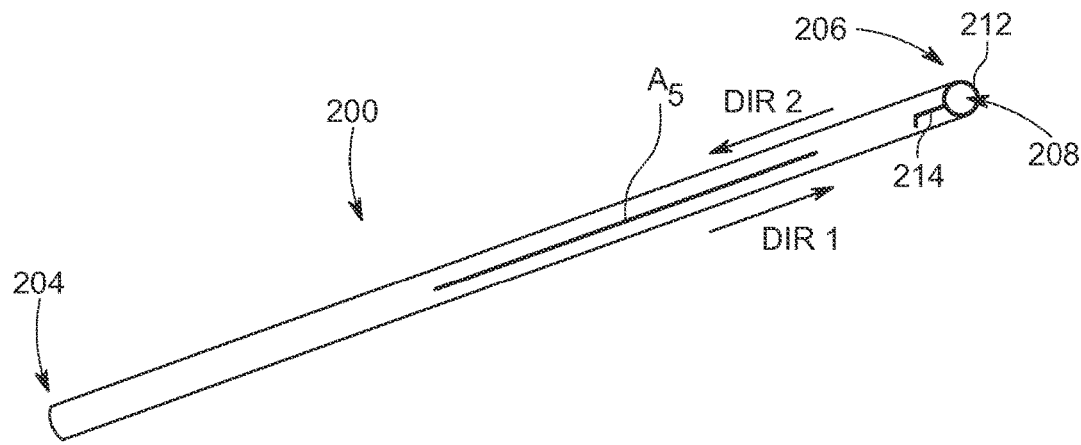
FIG. 25 is a perspective view of a trocar having a distal end with a needle point slot that follows a tortuous path, in accordance with one embodiment of the present patent application.
Figures 26A, 26B:
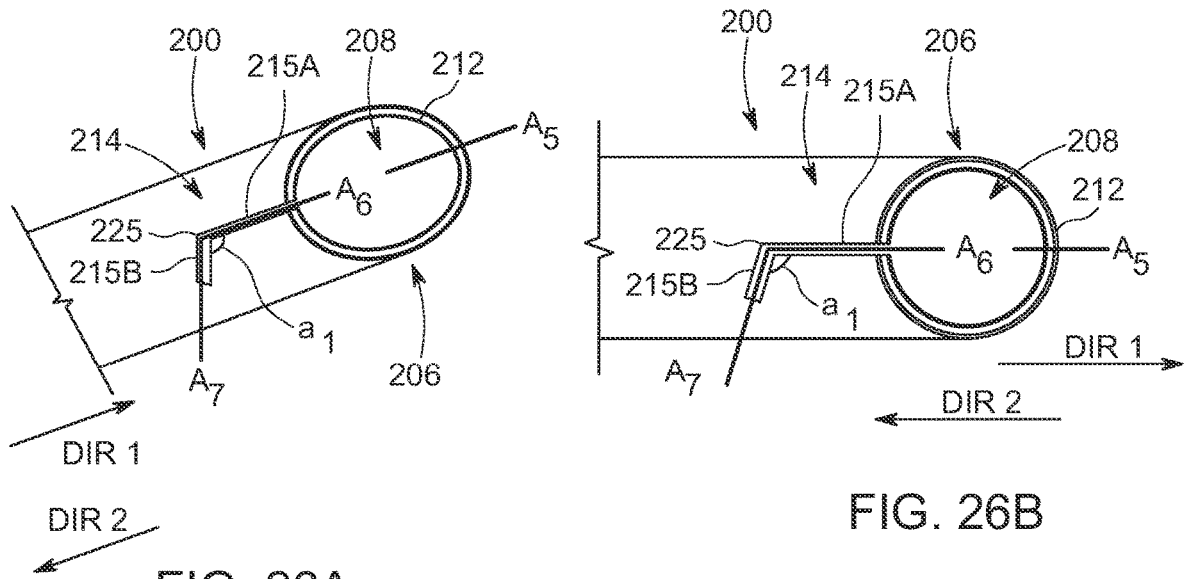
FIG. 26A is a magnified view of the distal end of the trocar shown in FIG. 25.
FIG. 26B is a second magnified view of the distal end of the trocar shown in FIG. 25.
Figure 26C:
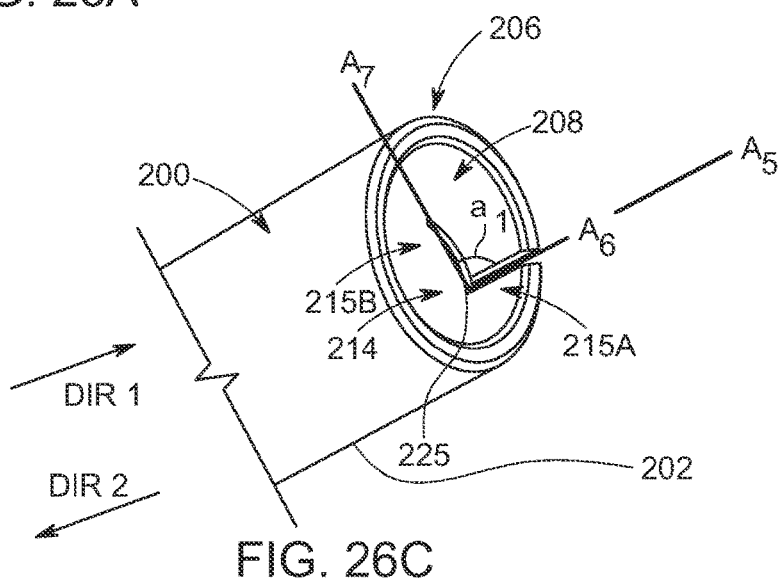
FIG. 26C is a third magnified view of the distal end of the trocar shown in FIG. 25.

FIG. 24 shows the suture needle 118 and the suture thread 125 attached to the suture needle after both components have been completely withdrawn from a proximal opening at the proximal end 104 of the tubular shaft 102 of the needle sheath 100. A section of the suture thread 125 is secured between the first and second clamping jaws 138, 140 of the needle driver 130. After the suture needle 118 is withdrawn from the proximal end 104 of the tubular shaft 102 of the needle sheath 100, it transforms back to its normal, curved shape.

In one embodiment, one or more of the structural features incorporated into the needle sheaths disclosed herein may be incorporated into surgical trocars. Referring to FIGS. 25 and 26A-26C, in one embodiment, a trocar 200 is configured for safely and effectively delivering a suture needle to a surgical site and, after completing a surgical procedure, withdrawing the suture needle from the surgical site for being removed from a patient's body. The trocar may be made of rugged, biocompatible materials such as polymers and metals (e.g., stainless steel). In one embodiment, the trocar 200 desirably includes a tubular shaft 202 having a proximal end 204 and a distal end 206. The tubular shaft 202 is preferably hollow for passing suture needles therethrough and desirably has an elongated conduit 208 that extends from the proximal end 204 to the distal end 206 thereof. In one embodiment, the trocar 200 preferably has a longitudinal axis $A_5$ that extends from the proximal end 204 to the distal end 206 of the tubular shaft 202. In one embodiment, the distal end 206 of the tubular shaft 202 desirably has a chamfered edge 212. In one embodiment, the chamfered edge 212 preferably defines a distal-most end of the tubular shaft 202 of the trocar 200.

In one embodiment, the trocar 200 desirably includes a needle point slot 214 that is formed in the outer wall of the tubular shaft 202. The needle point slot 214 preferably follows a tortuous path. As used herein, the terminology tortuous path means paths that are twisting, turning, bending, winding, crooked, circuitous, and/or non-linear. The tortuous path 214 may have three dimensions as it extends proximally through the outer wall of the tubular shaft. In one embodiment, the needle point slot 214 following a tortuous path may have a first section 215A having a length that extends along a first section longitudinal axis $A_6$, which is parallel with the longitudinal axis $A_5$ of the trocar 200, and a second section 215B having a length that extends along a second section longitudinal axis $A_7$, which defines an obtuse angle α1 relative to the first section longitudinal axis $A_6$. The tortuous path of the needle point slot 214 may have any geometry that does not provide a continuous, straight-line path to the opening at the distal end of the trocar 200. In one embodiment, the tortuous path 214 includes an angled corner 225 (FIG. 26B) that is located between the first and second sections 215A, 215B of the needle point slot 214, which forces the needle to change direction and thereby prevents the needle from springing out from opening at the distal end 206 of the tubular shaft 202 of the trocar 200

In one embodiment, the chamfered edge 212 of the trocar 200 may project from a bottom side of the tubular shaft 202 and the needle point slot 214 may be formed on a top side of the tubular shaft, whereby the needle point slot 214 is about 180 degrees away from the chamfered edge 212 about the circumference of the outer wall of the tubular shaft 202.

In one embodiment, during needle pull out through the trocar 200, the needle point slot 214 with the tortuous path allows the needle point of a suture needle to slide easily in a proximal direction DIR2 toward the proximal end of the trocar 200. If, during retraction, the needle is accidently released before being completely retracted into the trocar 200, the spring back motion of the needle in the distal direction DIR1 will be stopped by the tortuous path of the needle point slot 214.

Figure 27:
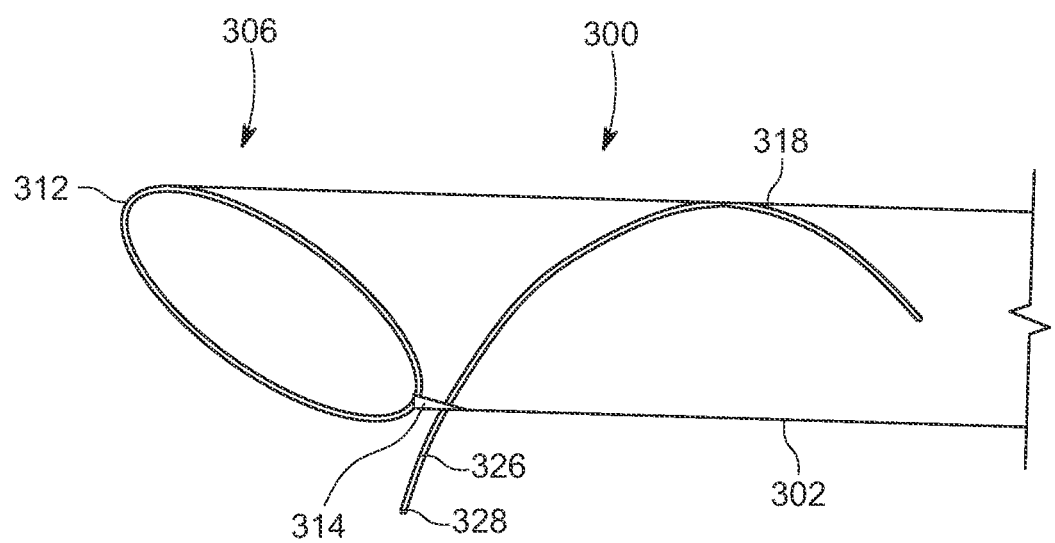
FIG. 27 is a schematic view of a distal end of a trocar having a tapered needle point slot, in accordance with one embodiment of the present patent application.

Referring to FIG. 27, in one embodiment, a trocar 300 may include a tubular shaft 302 having a distal end 306 with a chamfered edge 312 and a tapered notch 314 formed in the outer wall of the tubular shaft 302. The tapered notch 314 is configured to catch the needle point 428 or the distal end 426 of a surgical needle 318 so that the needle is secured to the trocar and cannot be expelled from the distal end 306 of the tubular shaft 302.

Figure 28:
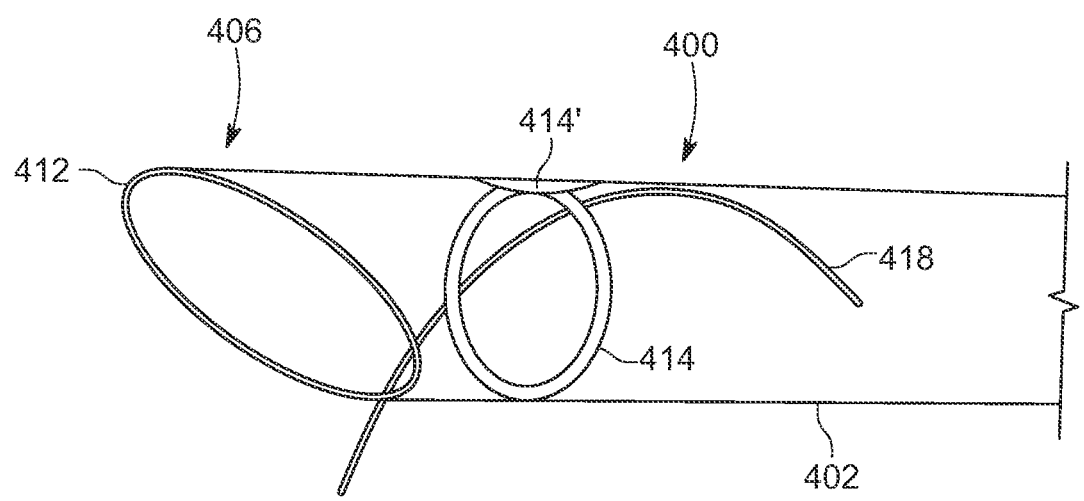
FIG. 28 is a schematic view of a distal end of a trocar having an internal stop ring, in accordance with one embodiment of the present patent application.

Referring to FIG. 28, in one embodiment, a trocar 400 may include a tubular shaft 402 having a distal end 406 with a chamfered edge 412 and a stop ring 414 extending inwardly from the outer wall of the tubular shaft 402. The stop ring 414 preferably has a smaller diameter than the inner diameter of the outer wall of the tubular shaft 402. During needle pull-out, the stop ring 414 is preferably configured to catch a surgical needle 418 so that the needle cannot be expelled from the distal end of the tubular shaft 402.

Referring to FIG. 28, in one embodiment, a trocar 400 may have a stop bump 414' extending inwardly from the outer wall of the tubular shaft 402. The stop bump 414' preferably defines a reduced diameter section inside the tubular shaft 402. During needle pull-out, the stop bump 414' is preferably configured to catch the surgical needle 418 so that the needle cannot be expelled from the distal end of the tubular shaft 402.

In one or more embodiments, any of the needle control features disclosed in the embodiments of FIGS. 25-28, including the needle point slot 214 with the tortuous path (FIG. 25), the tapered notch 314 (FIG. 27), the stop ring 414 (FIG. 28), and the stop bump 414' (FIG. 28) may be incorporated into any of the needle sheath embodiments disclosed herein While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A needle sheath comprising:
   a tubular shaft having a proximal end, a distal end, and a longitudinal axis that extends from the proximal end to the distal end of said tubular shaft, wherein said tubular shaft is hollow and includes a proximal opening located at the proximal end of said tubular shaft, a distal opening located at the distal end of said tubular shaft, and an elongated conduit that extends between the proximal and distal openings:
   a stop flange secured to the proximal end of said tubular shaft;
   the distal end of said tubular shaft including a chamfered edge located on a bottom side of said tubular shaft;
   a needle relief slot formed in the bottom side of said tubular shaft, said needle relief slot being proximal to said chamfered edge and having a length that extends along an axis that is parallel with the longitudinal axis of said tubular shaft;
   a needle point slot formed in a top side of said tubular shaft, wherein said needle point slot opposes said needle relief slot formed in the bottom side of said tubular shaft.

2. The needle sheath as claimed in claim 1, wherein the axis of said needle relief slot intersects with said chamfered edge of said tubular shaft.

3. The needle sheath as claimed in claim 1, wherein said needle point slot is distal to said needle relief slot.

4. The needle sheath as claimed in claim 3, wherein said needle point slot has a length that extends along an axis that is perpendicular to the longitudinal axis of said tubular shaft.

5. The needle sheath as claimed in claim 1, wherein said tubular shaft comprises a cylindrical shaped outer wall defining inner and outer surfaces, and wherein said needle relief slot is formed in said cylindrical shaped outer wall and extends from the inner surface to the outer surface of said cylindrical shaped outer wall.

6. The needle sheath as claimed in claim 5, wherein said needle point slot is formed in said cylindrical shaped outer wall and extends from the inner surface to the outer surface of said cylindrical shaped outer wall.

7. The needle sheath as claimed in claim 6, further comprising a suture needle disposed within said tubular shaft, wherein said suture needle has a curved body disposed within said needle relief slot and a needle point disposed in said needle point slot.

8. The needle sheath as claimed in claim 7, wherein said curved body of said suture needle extends outside said tubular shaft, and wherein said suture needle defines a first height that is greater than a cross-sectional diameter of said tubular shaft of said needle sheath.

9. The needle sheath as claimed in claim 8, wherein said suture needle comprises a superelastic material that enables said curved body of said suture needle to transform from a curved configuration having the first height to a flatter configuration having a second height that is less than the first height and that is less than an inner diameter of said tubular shaft of said needle sheath.

10. The needle sheath as claimed in claim 7, further comprising a suture thread secured to a proximal end of said suture needle.

11. The needle sheath as claimed in claim 10, further comprising a needle driver disposed within said elongated conduit of said tubular shaft of said needle sheath, wherein said needle driver comprises clamping jaws in contact with at least one of said suture needle and said suture thread secured to the proximal end of said suture needle.

12. The needle sheath as claimed in claim 1, wherein said tubular shaft has an outer diameter, and wherein said stop flange has an outer diameter that is greater than the outer diameter of said tubular shaft.

13. The needle sheath as claimed in claim 1, wherein said needle sheath comprises durable, biocompatible materials selected from the group consisting of polymers, metals, and stainless steel.

14. A needle sheath comprising:
   a tubular shaft having a proximal end, a distal end with a chamfered edge, and a longitudinal axis extending between the proximal and distal ends of said tubular shaft;
   a flange secured to the proximal end of said tubular shaft having an outer dimension that is greater than a cross-sectional diameter of said tubular shaft;
   a needle relief slot formed in a bottom side of said tubular shaft, wherein said needle relief slot has a length that extends along a needle relief slot axis that is parallel to the longitudinal axis of said tubular shaft and that passes through said chamfered edge:
a needle point slot formed in a top side of said tubular shaft that is distal to said needle relief slot, wherein said needle point slot has a length that extends along a needle point slot axis that is perpendicular to both the longitudinal axis of said tubular shaft and the needle relief slot axis of said needle relief slot.

15. The needle sheath as claimed in claim 14, further comprising a suture needle disposed within said tubular shaft of said needle sheath, wherein said suture needle has a curved body disposed within said needle relief slot and a needle point disposed in said needle point slot.

16. The needle sheath as claimed in claim 15, wherein said curved body of said suture needle passes through said needle relief slot for extending outside said tubular shaft of said needle sheath, and wherein said curved body of said suture needle defines a first height that is greater than the cross-sectional diameter of said tubular shaft.

17. The needle sheath as claimed in claim 16, wherein said suture needle comprises a superelastic material that enables said suture needle to transform from a curved configuration having the first height to a flatter configuration having a second height that is less than the first height, wherein the second height is less than or equal to an inner diameter of said tubular shaft of said needle sheath.

18. The needle sheath as claimed in claim 17, further comprising:
a suture thread secured to a proximal end of said suture needle; and
a needle driver disposed within said tubular shaft of said needle sheath, wherein said needle driver comprises clamping jaws in contact with at least one of said suture needle and said suture thread secured to the proximal end of said suture needle.

19. A surgical tool for introducing and removing a suture needle from a surgical cavity comprising:
a tubular shaft having a proximal end with a proximal opening, a distal end with a distal opening, and a longitudinal axis that extends from the proximal end to the distal end of said tubular shaft;
the distal end of said tubular shaft including a chamfered edge located on a bottom side of said tubular shaft;
a needle relief slot formed in the bottom side of said tubular shaft, said needle relief slot being proximal to said chamfered edge and having a length that extends along an axis that is parallel with the longitudinal axis of said tubular shaft:
a suture needle stop formed in a top side of said tubular shaft for preventing uncontrolled release of said suture needle from the distal opening at the distal end of said tubular shaft, wherein said suture needle stop is formed in an inner surface of said tubular shaft and opposes said chamfered edge of said tubular shaft, and wherein said needle point stop is distal to said needle relief slot.

20. The surgical tool as claimed in claim 19, wherein said surgical tool is selected from the group of surgical tools consisting of trocars and needle sheaths.

21. The surgical tool as claimed in claim 19, wherein said suture needle stop formed in the inner surface of said tubular shaft is selected from the group consisting of needle point slots having tortuous paths, tapered notches, stop rings that project inwardly from the inner surface of said tubular shaft, and stop bumps that project inwardly from the inner surface of said tubular shaft.

22. A needle sheath comprising:
a tubular shaft having a proximal end, a distal end, and a longitudinal axis that extends from the proximal end to the distal end of said tubular shaft;
a stop flange secured to the proximal end of said tubular shaft;
the distal end of said tubular shaft including a chamfered edge located on a bottom side of said tubular shaft;
a needle relief slot formed in the bottom side of said tubular shaft, said needle relief slot being proximal to said chamfered edge and having a length that extends along an axis that is parallel with the longitudinal axis of said tubular shaft;
a needle point slot formed in a top side of said tubular shaft, wherein said needle point slot opposes said needle relief slot formed in the bottom side of said tubular shaft, and wherein said needle point slot is distal to said needle relief slot.

* * * * *